(12) United States Patent
Sims, Jr.

(10) Patent No.: US 10,092,675 B1
(45) Date of Patent: Oct. 9, 2018

(54) WEAR-RESISTANT JOINT ARTHROPLASTY IMPLANT DEVICES

(71) Applicant: Dewey M Sims, Jr., Royal Oak, MI (US)

(72) Inventor: Dewey M Sims, Jr., Royal Oak, MI (US)

( * ) Notice: Subject to any disclaimer, the term of this patent is extended or adjusted under 35 U.S.C. 154(b) by 0 days.

(21) Appl. No.: 15/675,724

(22) Filed: Aug. 12, 2017

(51) Int. Cl.
| | |
|---|---|
| *A61L 27/10* | (2006.01) |
| *A61L 27/16* | (2006.01) |
| *A61L 27/18* | (2006.01) |
| *A61F 2/30* | (2006.01) |
| *A61L 27/50* | (2006.01) |

(52) U.S. Cl.
CPC .......... *A61L 27/10* (2013.01); *A61F 2/30965* (2013.01); *A61L 27/16* (2013.01); *A61L 27/18* (2013.01); *A61L 27/50* (2013.01); *A61F 2002/30026* (2013.01); *A61F 2310/00329* (2013.01); *A61L 2430/24* (2013.01)

(58) Field of Classification Search
None
See application file for complete search history.

(56) References Cited

U.S. PATENT DOCUMENTS

| | | | | |
|---|---|---|---|---|
| 4,963,151 A | * | 10/1990 | Ducheyne | .......... A61B 17/8802 428/297.4 |
| 6,686,437 B2 | | 2/2004 | Buchman et al. | |
| 6,987,136 B2 | * | 1/2006 | Erbe | ...................... A61L 27/446 424/423 |
| 9,445,916 B2 | | 9/2016 | Baa et al. | |
| 9,605,134 B2 | | 3/2017 | Doering et al. | |
| 2005/0043815 A1 | * | 2/2005 | King | .......................... A61F 2/34 623/23.58 |

(Continued)

*Primary Examiner* — Peter A Salamon
(74) *Attorney, Agent, or Firm* — Mastrogiacomo PLLC

(57) ABSTRACT

A prosthesis for a synovial joint arthroplasty within a human body is provided. The prosthesis includes a first prosthetic component, the first prosthetic component including a first surface and the first prosthetic component is formed of a plastic compound, the plastic compound includes a polymer, a plurality of long glass fibers, the long glass fibers being randomly dispersed throughout the polymer to improve surface fatigue life and inhibit surface crack propagation to the prosthesis and improve wear resistance of the prosthesis, a number of the plurality of long glass fibers configured to protrude outward from the first surface of the first prosthetic component, a plurality of beads, the beads being randomly dispersed throughout the polymer to improve surface fatigue life and inhibit surface crack propagation to the prosthesis and improve wear resistance of the prosthesis, a number of the plurality of beads configured to protrude outward from the first surface of the first prosthetic component, a second prosthetic component, the second prosthetic component including a second surface, the second surface of the second prosthetic component configured to engage said first surface of said first prosthetic component and slide relative to the first surface of the first prosthetic component while contacting the plurality of long glass fibers protruding outward from the first surface of the first prosthetic component and the plurality of beads protruding outward from the first surface of the first prosthetic component.

21 Claims, 20 Drawing Sheets

(56) References Cited

U.S. PATENT DOCUMENTS

| | | | |
|---|---|---|---|
| 2007/0111165 A1* | 5/2007 | Wallick | A61C 8/0012 433/212.1 |
| 2008/0133018 A1* | 6/2008 | Salovey | A61F 2/30 623/18.11 |
| 2010/0168798 A1* | 7/2010 | Clineff | A61L 27/446 606/279 |

* cited by examiner

WEAR-RESISTANT JOINT ARTHROPLASTY IMPLANT DEVICES

CROSS REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON COMPACT DISC

Not Applicable

BACKGROUND OF THE INVENTION

1. Field of the Invention

The present invention relates generally to an arthroplasty to replace a musculoskeletal joint and, more particularly, to the improvements in materials used in medical implant devices that are used in the arthroplasty.

2. Background Art

Within the human body, a natural joint is the connection between two bones. There are several types of joints in the human body that ensure proper movement. The joints may be categorized into load bearing and non-load bearing joints. Joints in the knee, hip, shoulder, ankle and intervertebral disc in the spine, among others, are considered to be load bearing joints. Joints in the fingers and toes are considered to be non-load bearing joints. Further, joints having a joint cavity, which constitute the free movable joints of the body, are call the synovial joints. Joints in the knee, hip, shoulder and ankle are characterized as synovial joints. The intervertebral disc is a cartilaginous joint. These joints may undergo degenerative changes due to disease, age, trauma, repetitive loading and unloading and/or genetics.

Joint replacement surgery or replacement arthroplasty has been used by orthopedic surgeons over the last several decades to treat patients that have sever joint degeneration due to one or more of the degenerative changes described above. Arthroplasty is a procedure in which the dysfunctional joint is replaced with an orthopedic prosthesis. Arthroplasty is considered when less intrusive measures to alleviate the joint dysfunction, such as pain medications, have been exhausted.

The most common joint replacement surgeries are hip arthroplasty, knee arthroplasty, shoulder arthroplasty and disc arthroplasty. These joints are subject to arthritis or dysfunction because they are often the joints within the body that are under the most stress. The constant loading and unloading of these joints is an everyday occurrence. The stress on these joints increases if one is an athlete, a participant in some athletic exercise on a daily basis over a number of years or their employment requires some level of manual labor. Also, the simple fact that many are living longer lives and the constant loading and unloading of these joints through every day tasks may lead to joint dysfunction. Further, dysfunction in the joint may be due to some other disease, trauma and/or genetics.

The prosthetic implants that have been developed to replace the dysfunctional joint are meant to mimic the function of the body's own structures. For example, a hip prosthesis may include both a ball and cup or socket. The prosthetic ball is secured to the femur and the prosthetic cup or socket to the acetabulum. The prosthetic ball is mated to the prosthetic cup to mimic a healthy hip joint. A knee prosthesis may include a prosthetic implant attached to the femur and a second prosthetic implant attached to the tibia to replace the damaged bone portion and mimic the ends of a healthy femur and tibia. A third prosthetic implant may be used to mimic the cartilage of the knee that has deteriorated. Similar prosthetic implants may be used in a shoulder arthroplasty, an ankle arthroplasty or disc arthroplasty to alleviate dysfunctional issues in those areas of the body.

Many different types of material have been used in the development of the prosthesis used in an arthroplasty. The most popular materials used for the alternative bearing surfaces of the interacting prosthetic implants include metal-on-metal, ceramic-on-ceramic, metal-on-polyethylene and ceramic-on-polyethylene. Presently, ultra high molecular weight polyethylene ("UHMWPE") is the polymer material of choice. A chart illustrating the percentage use of the alternative bearings between 2005 and 2012 is included in FIG. 13.

Joint replacement of the hip ball and socket interface is very common these days. The hip joint is different from any other load-bearing joint because it has a large wear contact area and because this joint is loaded and unloaded as you walk. The constant loading and unloading of the joint may lead to high stress concentration areas within the prosthetic hip joint and may lead to failure of one or both of the implants.

High stress concentration on the inside of the cup may cause creep problems. Creep is plastic deformation surface damage caused by high stresses. The head of the ball penetration into the cup or socket may cause microseparation and edge loading. Accelerated wear of each prosthetic component may also be caused by high stresses. Microseparation and edge loading may lead to surface and subsurface stress and strain at the rim of a UHMWPE acetabular cup. The high stress concentration along the rim of the acetabular cup may cause the rim of the acetabular cup to fail leading to overall failure of the prosthetic joint and further surgeries to replace the prosthetic components.

Knee arthroplasty is also a common orthopedic surgery these days to alleviate pain and repair the knee joint. The knee joint is under constant weight and stress as one walks, runs, climbs stairs, etc. Along with the hip joint, the knee joint contact area is also a very high stressed contact area. The prosthetic knee joint may typically include a first metal implant secured to the femur, a second metal implant secured to the tibia and a piece of polyethylene positioned between the two metal implants to mimic the body's own cartilage and cushion the contact between the two metal implants. If the prosthetic implants of the knee joint are not positioned properly or the implants begin to breakdown after a number of years, a high stress concentration may occur within the polyethylene and cause the polyethylene component to fail. Further, severe delamination of an Ortholoc tibial component may be caused by high stresses. Also, high stress concentration on the surface of the tibial component may cause pitting and delamination. Still further, sever wear problems may be a result of crack initiation and crack propagation that may be accelerated by high stresses within the polyethylene component leading to overall failure of the prosthetic joint and further surgeries to replace the prosthetic components.

The disc joint contact area of the back or spine is also a very high stressed contact area. The spine is constantly compressed and expanded as one moves. Cartilage between each vertebrae of the spine is under constant compression and expansion. This constant compression and expansion of the cartilage may introduce high stress areas. Disc arthroplasty aims to introduce prosthetic implants to repair any dysfunction disc joints. If an implant is incorrectly placed or there have been a number of years of regular use of the disc joint, the high stress concentrations along the rim of the prosthetic disc may cause the rim to fail. Further, burnishing, plastic deformation, transverse crack rim fracture failures of the polyethylene prosthetic component have been seen in as early as 4.9 years after the prosthetic implants have been introduced into the body. Still further, dome penetrations within the polyethylene prosthetic component due to high stresses may also occur all leading to overall failure of the prosthetic joint and further surgeries to replace the prosthetic components.

There have been some improvements to the materials used in prosthetic implants during the last several years. Most notably, the process of cross-linking polymers to improve the wear characteristics of the polymers used in prosthetic implants for the various joints has been developed. The cross-linking of polymers is generally completed through an irradiation process with an electron beam. A prosthetic component may undergo the irradiation process to improve wear characteristics. While the cross-linking of polymers has shown some improvement in the wear of prosthetic components, there are still issues with controlling the amount of irradiation to apply to a prosthetic component. This may lead to difficulty in identifying whether a component will wear longer than a non-cross-linked component. Also, most radiation penetrates only the surface. Once the cross-linked portion of the polymer at the surface has failed, the remainder of the component will fail as well. Furthermore, the radiation is expensive and a further step in the process is required to add Vitamin E to the polymer to improve oxidative stability leading to improved tensile and impact. Although there are cross-linking of the polymer does improve the wear characteristics of the prosthetic component, the components are still failing and further surgeries are needed to replace the prosthetic components.

Lubrication of the joints is also important to maintain the health of the natural joints by preventing cartilage wear under high loads in natural joints. Lubrication minimizes friction resistance between the bearing surfaces by keeping them apart. Synovial fluid is the lubricating fluid found in the synovial joints. The coefficient of friction in the synovial joint of a natural joint is typically in the range of 0.001 to 0.01. Within a prosthetic joint, generally the interface components are machined with such precision that there interface leaves little clearance for synovial fluid to enter and exit the joint. The coefficient of friction in the synovial joint of a prosthetic joint is typically in the range of 0.1 to 0.3 for polymer on polymer interfaces and 0.3 to 0.8 for metal on metal interfaces rendering these materials less than desirable substitutes for the natural joint.

Because of the loss of lubrication and increased friction of the prosthetic joint, the size of the prosthetic components relative to one another are limited to reduce the amount of surface area in contact between the prosthetic components thereby attempting to limit the friction torque in the joint. While the reduction in size of the prosthetic components works to limit the increase in friction between the mating prosthetic components, the reduction in size of the components also limits the range of motion in the joint. This may lead to dissatisfaction in the patient, especially one that may be physically active and may be restricted from activities due to the decreased range of motion from the prosthetic joint.

Due to the harsh environment of the human body fluids and the frequent movement of these parts, the useful lifetime of these implants may be from ten to twenty years and in some cases less than ten years (as discussed above). Thus a replacement is needed which involves repeated surgeries depending on the age of the patient.

Therefore, a need exists for weight bearing total joint arthroplasty implant devices having a high strength to stress ratio, biocompatibility, biodurability, low friction and low wear rate characteristics for high performance, longer life and lower risk of adverse responses such as particulate induced inflammation and osteolysis. There is also a need for such devices having articulating surfaces that do not produce potentially harmful metallic wear particulate. Ideally, known problems of using polymeric articulation surfaces, such as higher failure rates and the increased wear associated with strain hardening caused by multidirectional motion could also be overcome. Such devices are needed for applications requiring conformal bearing surfaces, such as an acetabular cup for a hip joint, and also for a high stress, non-conformal contact applications such as in a knee joint. Furthermore, such devices would also have a modulus of elasticity closer to the adjacent bone tissue to minimize the adverse effects of stress shielding on the adjacent bone. Still further, such devices would ensure that the prosthetic joint allow for the passage of an adequate amount of the body's lubricating fluid to reduce friction in the prosthetic joint, thereby leading to a longer wear life of more than 30 to 40 years and an increased range of motion over the prosthetic devices used in arthroplasty today.

BRIEF SUMMARY OF THE INVENTION

A prosthesis for a synovial joint arthroplasty within a human body is provided. The prosthesis includes a first prosthetic component, the first prosthetic component including a first surface and the first prosthetic component is formed of a plastic compound, the plastic compound includes a polymer, a plurality of long glass fibers, the long glass fibers being randomly dispersed throughout the polymer to improve surface fatigue life and inhibit surface crack propagation to the prosthesis and improve wear resistance of the prosthesis, a number of the plurality of long glass fibers configured to protrude outward from the first surface of the first prosthetic component, a plurality of beads, the beads being randomly dispersed throughout the polymer to improve surface fatigue life and inhibit surface crack propagation to the prosthesis and improve wear resistance of the prosthesis, a number of the plurality of beads configured to protrude outward from the first surface of the first prosthetic component, a second prosthetic component, the second prosthetic component including a second surface, the second surface of the second prosthetic component configured to engage said first surface of said first prosthetic component and slide relative to the first surface of the first prosthetic component while contacting the plurality of long glass fibers protruding outward from the first surface of the first prosthetic component and the plurality of beads protruding outward from the first surface of the first prosthetic component; and a gap, the gap created by the voids between the plurality of beads that protrude outward from the first surface of the first prosthetic component and between the plurality of long glass fibers that protrude outward from the first surface of the first prosthetic component, the gap further disposed between the first surface of the first prosthetic component and the second surface of the second prosthetic component to allow the passage of fluid between the first surface of the first prosthetic component and the second surface of the second prosthetic component.

BRIEF DESCRIPTION OF THE SEVERAL VIEWS OF THE DRAWINGS

The features and inventive aspects of the present invention will become more apparent from the following detailed description, claims, and drawings, of which the following is a brief description:

DETAILED DESCRIPTION OF THE INVENTION

Figure 1:
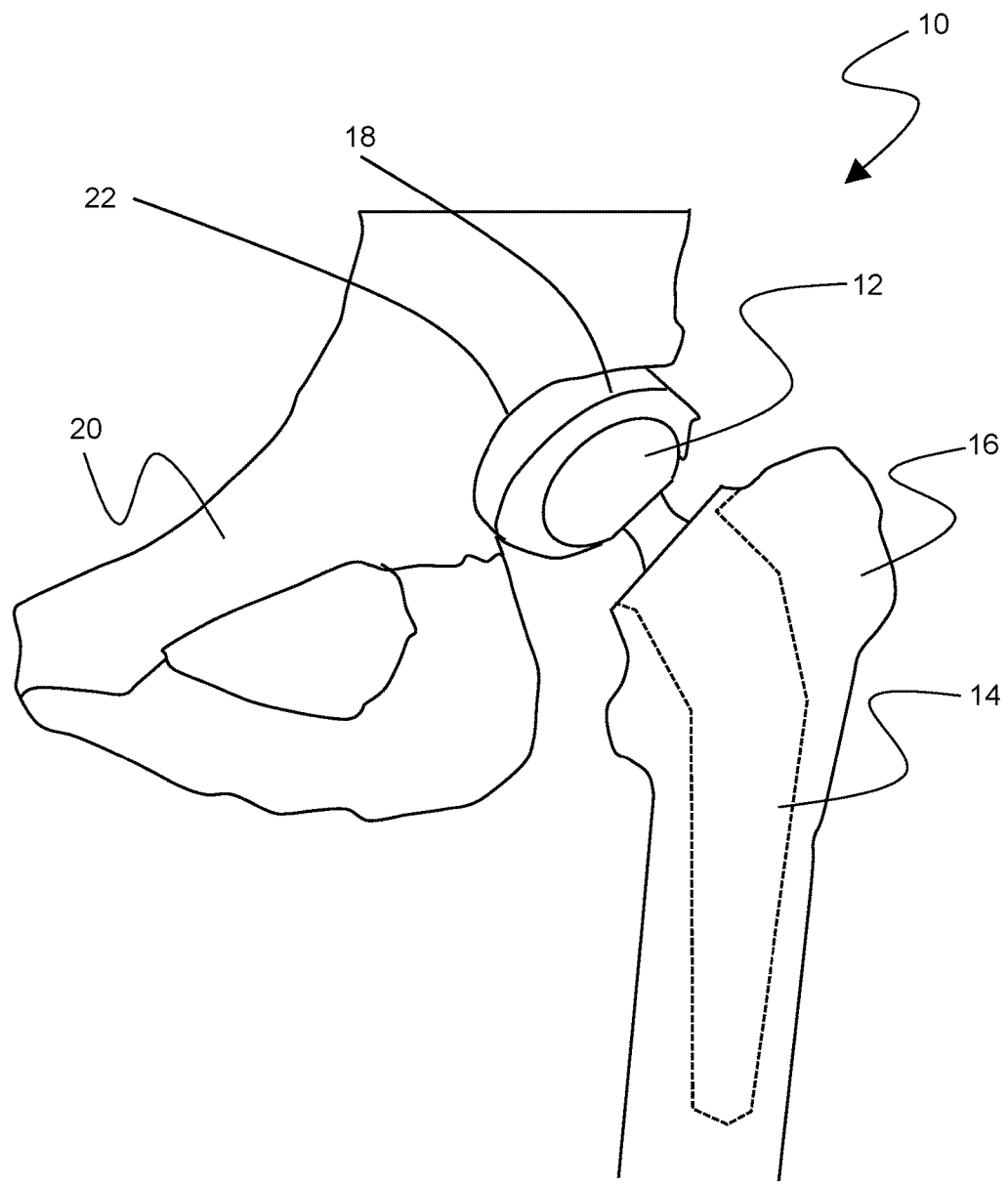
FIG. 1 is a perspective view of a hip joint illustrating the components of a prosthetic hip.
Figure 2:
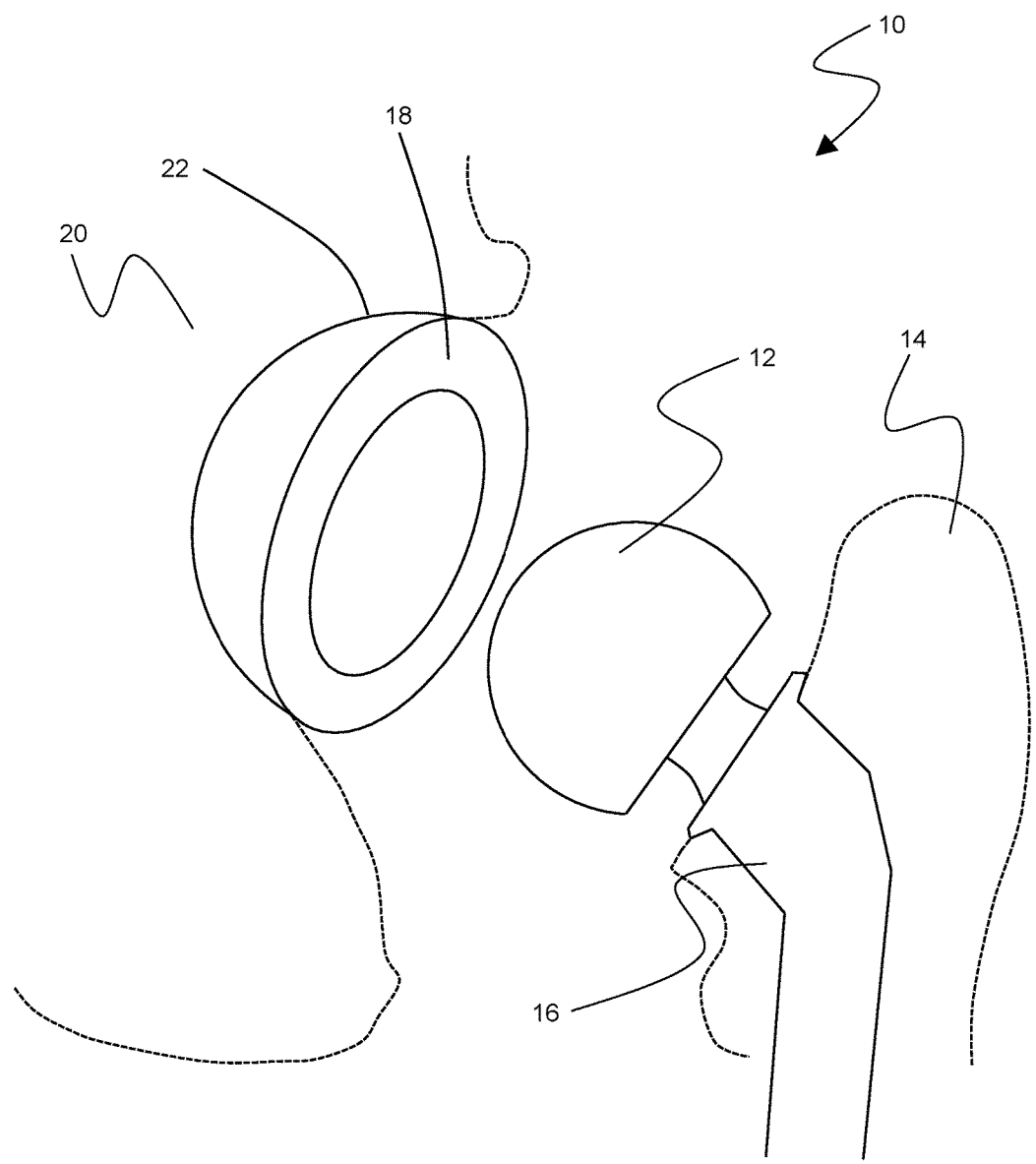
FIG. 2 is an enlarged view of the components of the prosthetic hip.
Figure 3A:
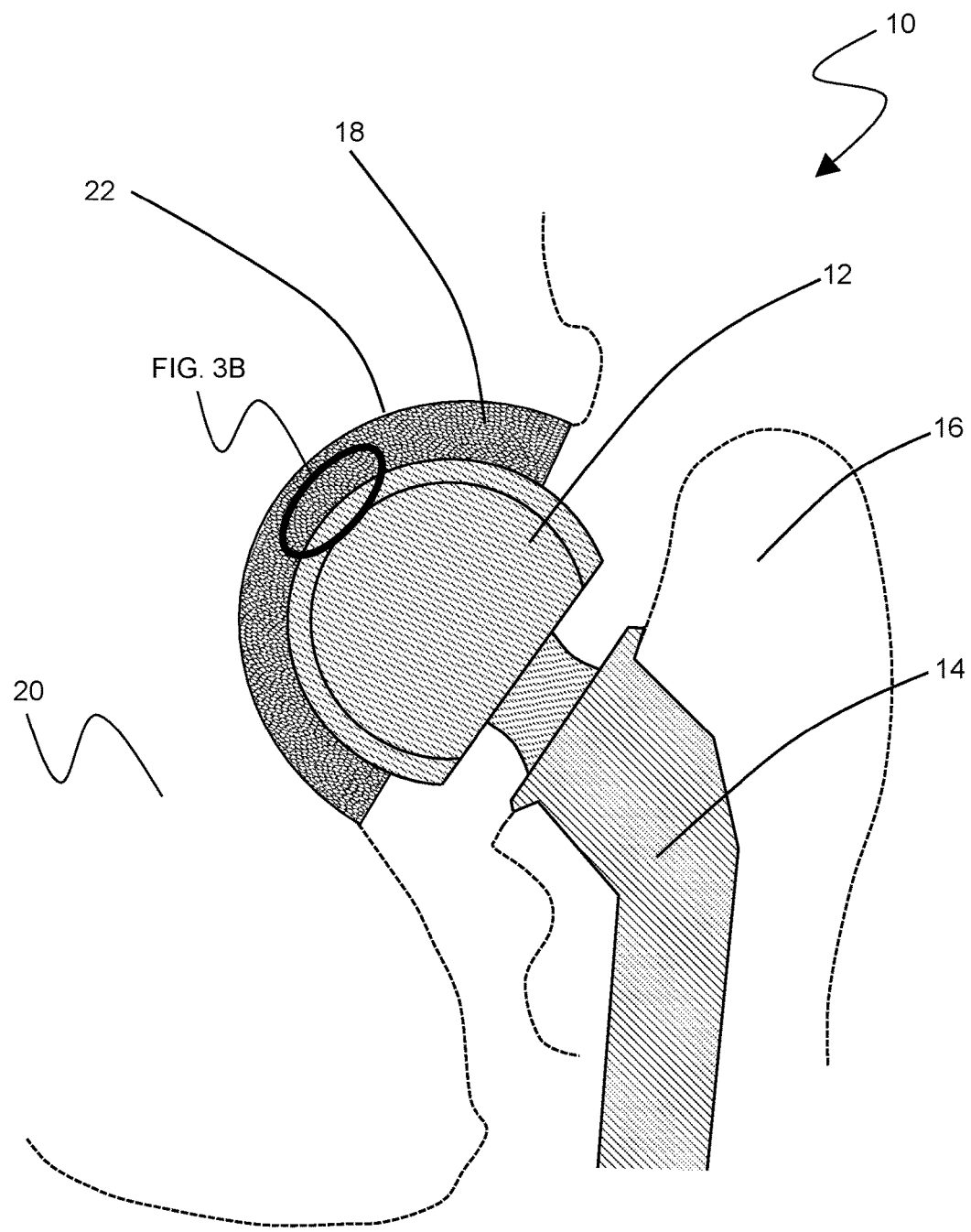
FIG. 3A is a cross-sectional view of the components of the prosthetic hip.
Figure 3B:
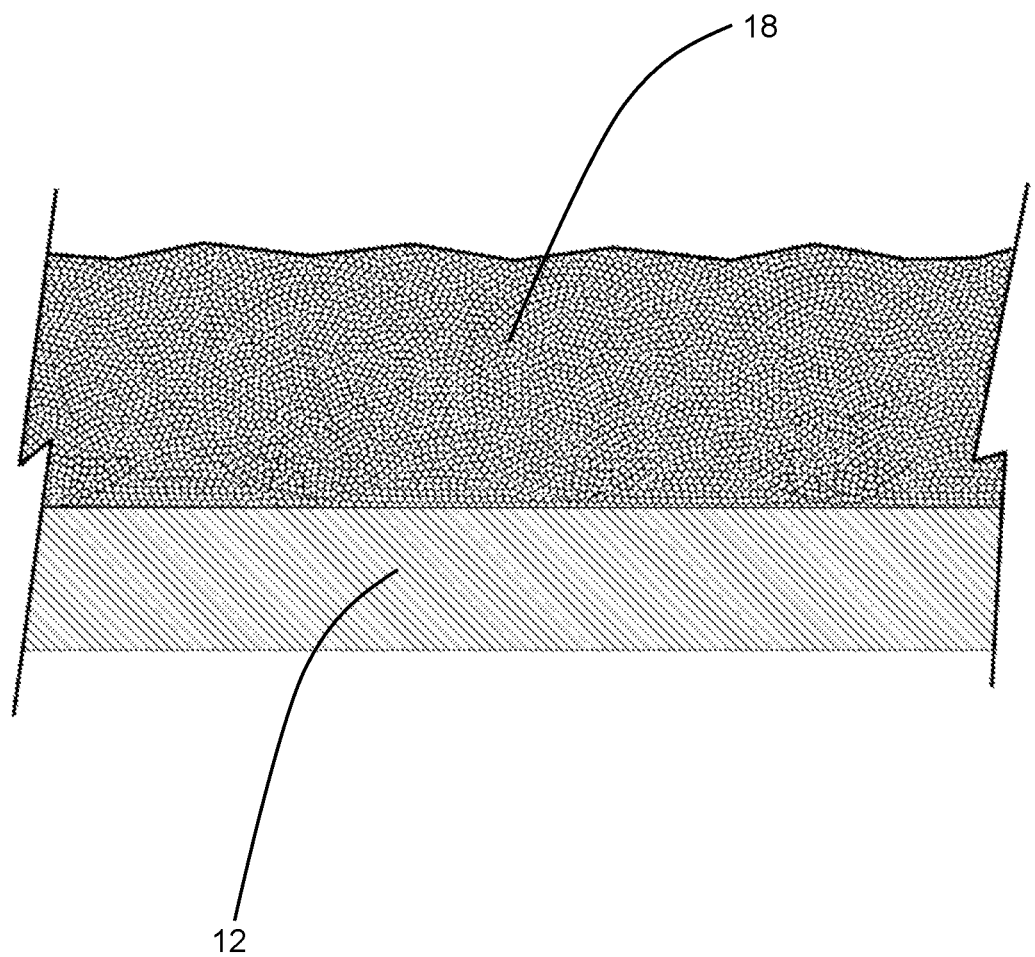
FIG. 3B in an enlarged view of the cross-section of FIG. 3A.

Referring now to the drawings, preferred illustrative embodiments of the present invention are shown in detail. Although the drawings represent embodiments of the present invention, the drawings are not necessarily to scale and certain features may be exaggerated to better illustrate and explain the present invention. Further, the embodiments set forth herein are not intended to be exhaustive or otherwise to limit or restrict the invention to the precise forms and configurations shown in the drawings and disclosed in the following detailed description.

Figure 8:
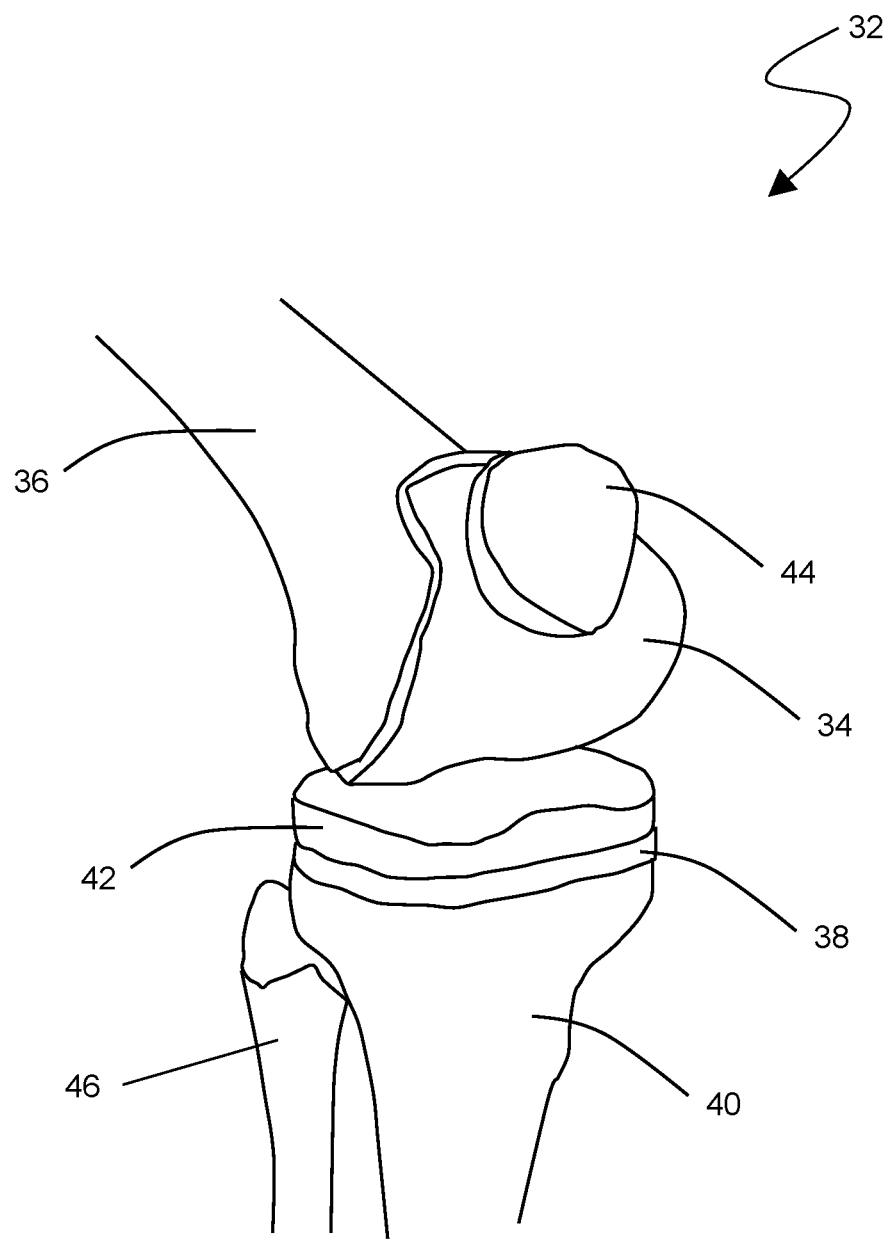
FIG. 8 is a perspective view of a knee joint illustrating the components of a prosthetic knee.
Figure 9:
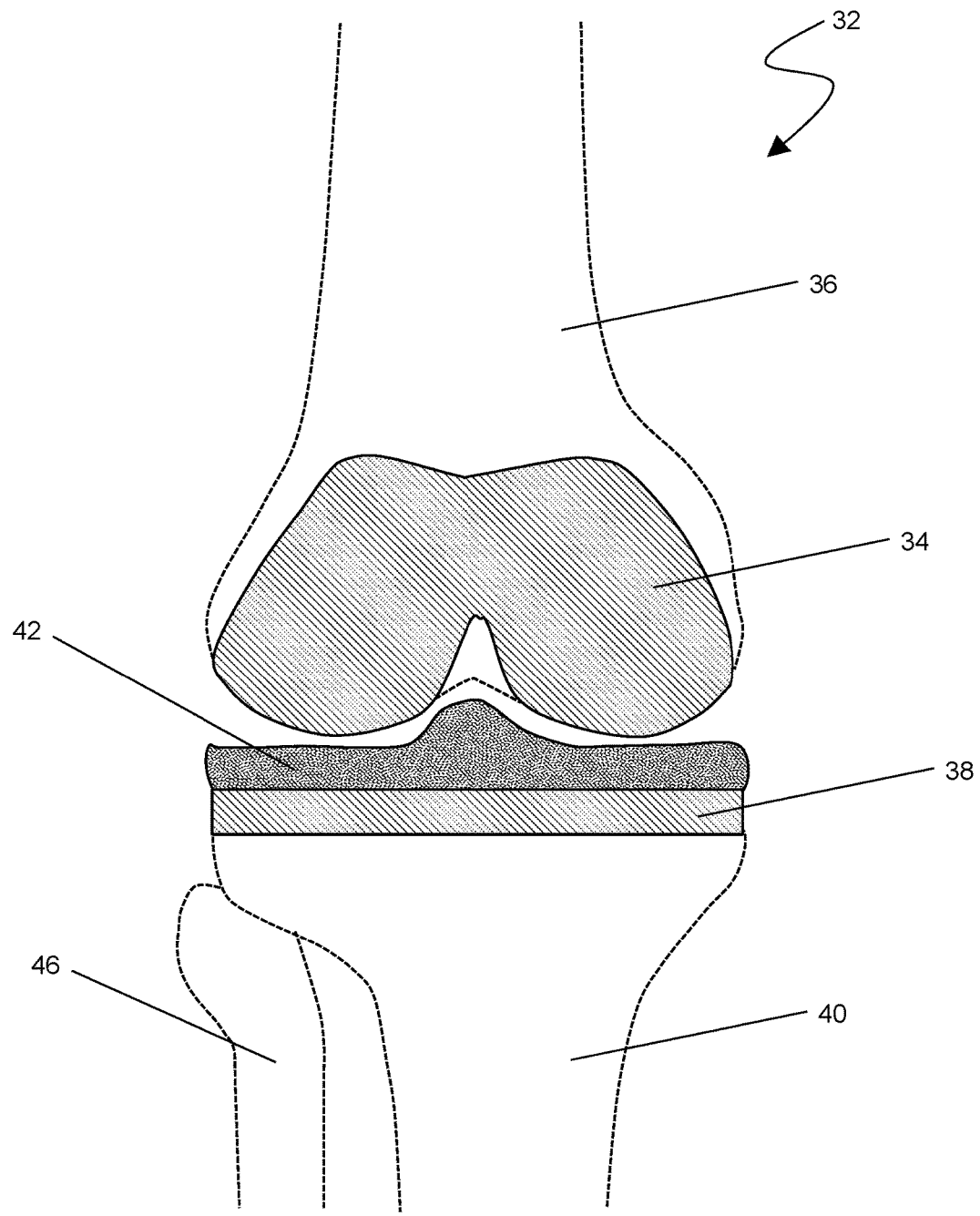
FIG. 9 is a cross-sectional view of the components of the prosthetic knee.
Figure 10:
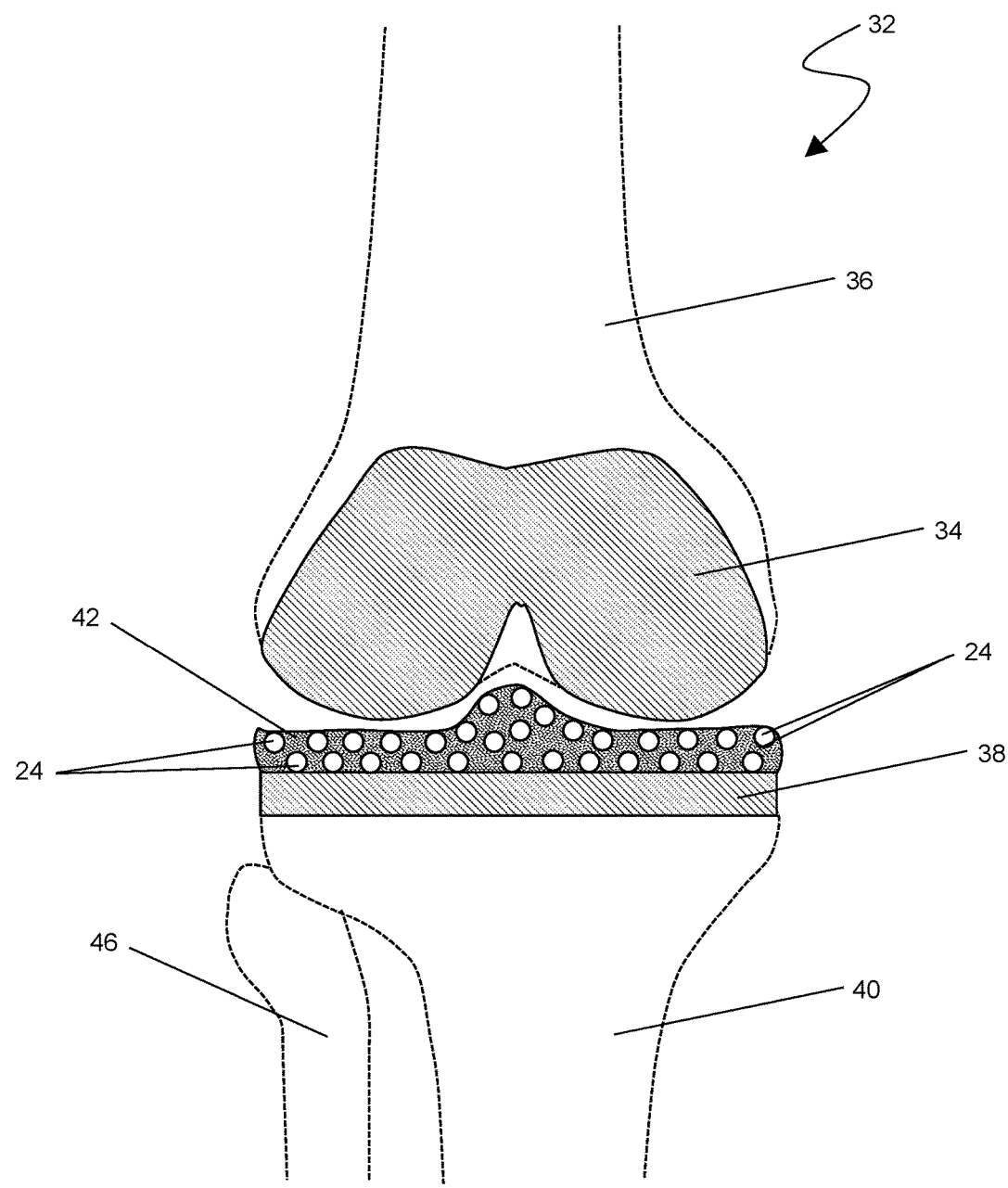
FIG. 10 is a cross-sectional view of the components of a prosthetic knee according to an embodiment of the present invention.
Figure 11:
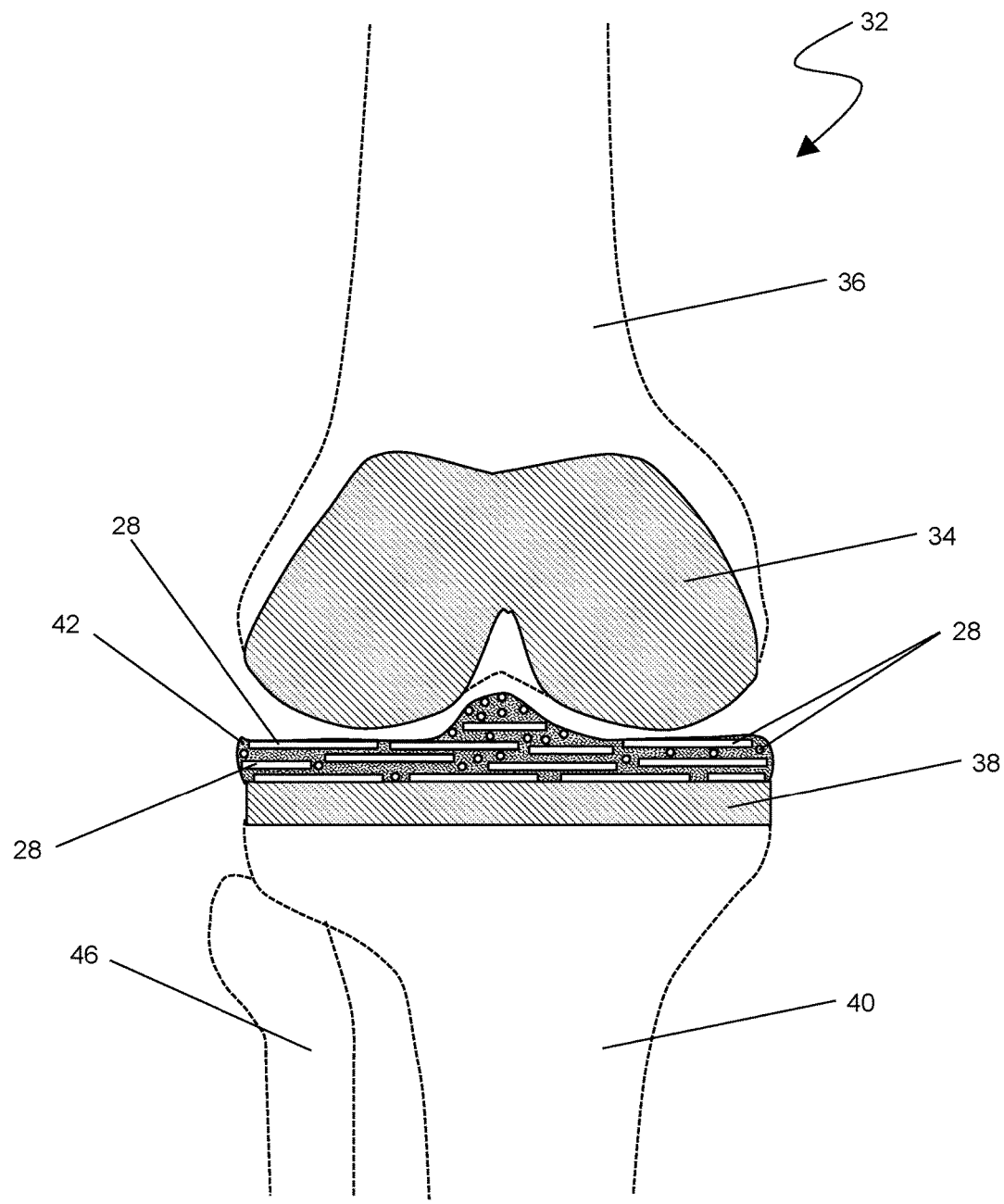
FIG. 11 is a cross-sectional view of the components of a prosthetic knee according to another embodiment of the present invention.
Figure 12:
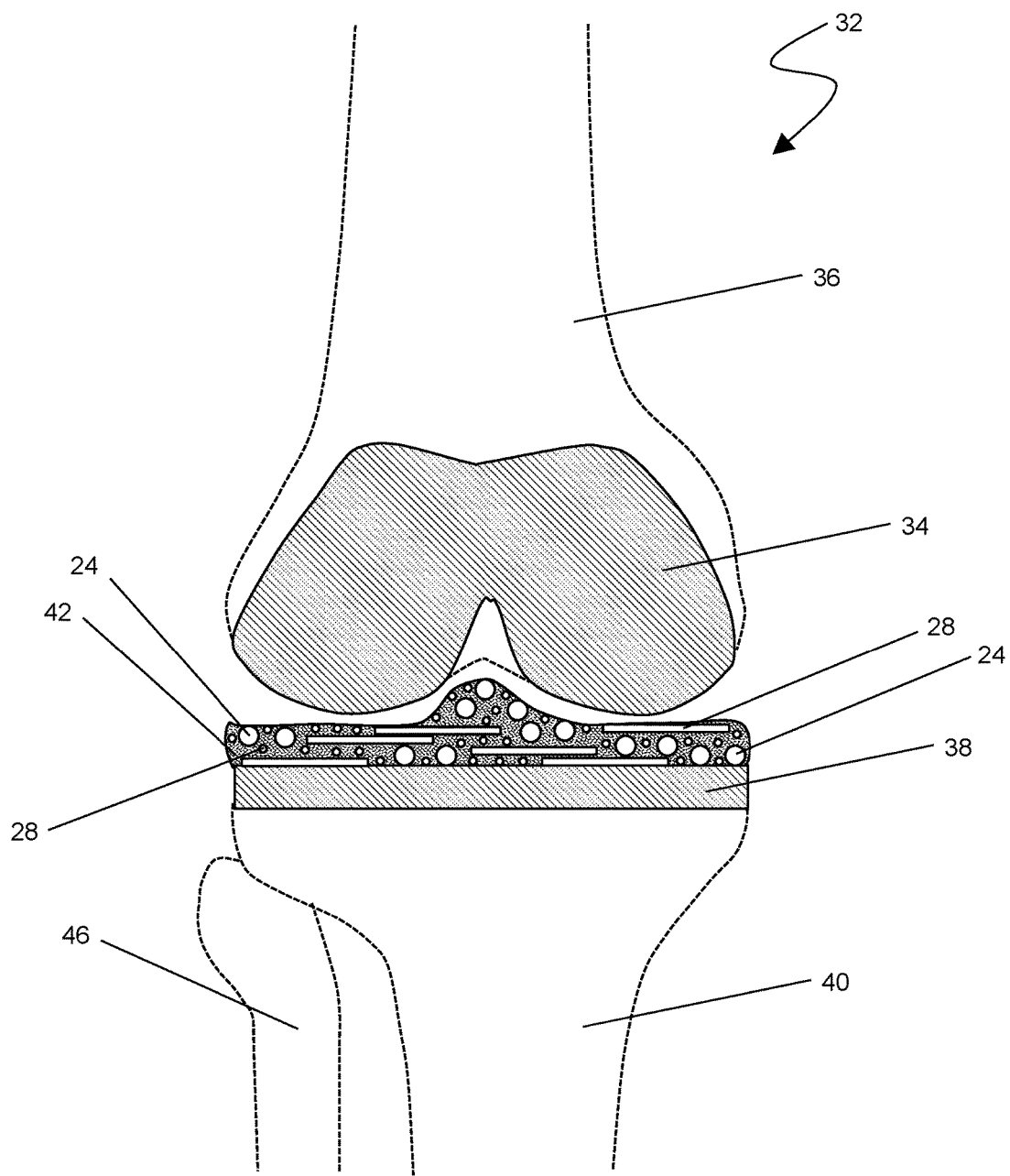
FIG. 12 is a cross-sectional view of the components of a prosthetic knee according to yet another embodiment of the present invention.

Joint replacement surgery or arthroplasty is a very common surgery that impacts several hundred thousand individuals each year. Joint Arthroplasty is becoming more and more commonplace as individuals live longer lives and the amount and intensity of athletic activity is ever increasing. FIGS. 1 and 8 illustrate two of the most common types of joint arthroplasty. FIG. 1 illustrated a hip joint and depicts a hip prosthesis and FIG. 8 illustrates a knee joint and depicts a knee prosthesis. As the number of joint replacement surgeries continue to increase, the quality of the materials used in the surgeries have improved as well. The materials used in joint replacement surgery or arthroplasty have been changed over the last several decades to improve wear characteristics and improve the life of the prosthetic implants.

Figure 13:
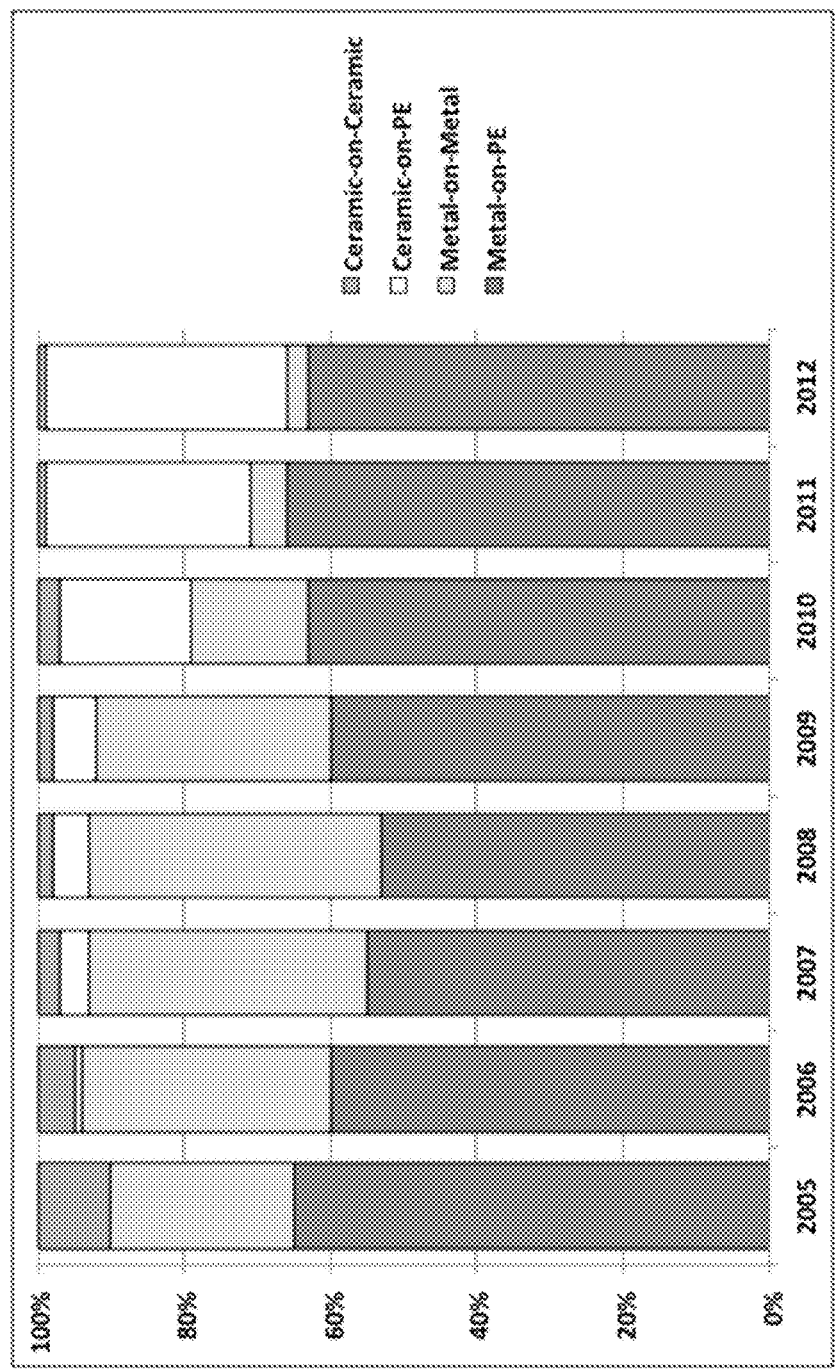
FIG. 13 is a chart that illustrates the different types of materials used in contemporary hip arthroplasty.

FIG. 13 is a chart that illustrates the different types of materials used in contemporary hip arthroplasty. The chart shows the percentage of the types of materials used versus a particular year, from 2005 through 2012. The different materials used in the hip arthroplasty include: ceramic (ball)-on-ceramic (cup), ceramic (ball)-on-polyethylene (cup), metal (ball)-on-metal (cup) and metal (ball)-on-polyethylene (cup). The most prevalent material combination used during that time frame for hip arthroplasty was metal (ball)-on-polyethylene (cup). The use of ceramic (ball)-on-polyethylene (cup) has increased steadily from 2006 onward at the expense of the metal (ball)-on-metal (cup) solution for hip arthroplasty. The cup or socket manufactured from polyethylene was used in over 80% of hip joint replacements in 2012 and is still the preferred solution today. Polyethylene is also one of the preferred prosthetic materials for use in other joint replacements as well.

Although polyethylene in its present state is a suitable material for prosthetic implants, it does have its drawbacks. Prosthetic implants manufactured of polyethylene do fail after a number of years due to the constant stress the implants undergo as an individual moves their body. A hip implant may last, on average, ten years depending on the individual and their lifestyle. A 60-year-old individual could have three to four joint replacement surgeries for the same implant just due to the wear rate of the materials used in the prosthetic joint today. To improve the longevity of the prosthetic implant, one could limit activity so as to limit the stresses on the implant. However this would impact the quality of life of the individual and would not be practical.

Another means to improve the longevity of the prosthetic implant is to improve the wear characteristics of the prosthetic components.

FIGS. 1-3A illustrate a hip joint 10 and depict a typical metal (ball)-on-polyethylene (cup) prosthesis. Generally a prosthetic metal ball 12 is supported by a stem 14 and is configured to replace the femoral head or "ball" and femoral neck of a femur 16. During the arthroplasty, the ball of the femur is removed and replaced with the prosthetic ball 12 and stem 14. Stem 14 is secured to femur 16 to position ball 12 in the location the natural ball of the femur had occupied. A prosthetic polyethylene cup or socket 18 may be configured to be secured to a pelvis 20 at an acetabulum 22. During the arthroplasty, the acetabulum is prepared to accept and secure the prosthetic cup to the pelvis. Prosthetic cup 18 will now act as the socket in the prosthetic ball-and-socket joint. Cup 18 may be sized to cooperatively seat ball 12. FIG. 3B is an enlarged cross-sectional view of the interface between cup 18 and ball 12. The prosthetic components of today are manufactured and finely machined in such a manner that the ball may fit precisely in the cup with virtually no space between the components and illustrated in FIG. 3B. With cup 18 secured to pelvis 20 at acetabulum 22, ball 12 may be introduced to cup 18 to form prosthetic hip joint 10 that mimics the look and function of a natural hip joint.

Figure 4A:
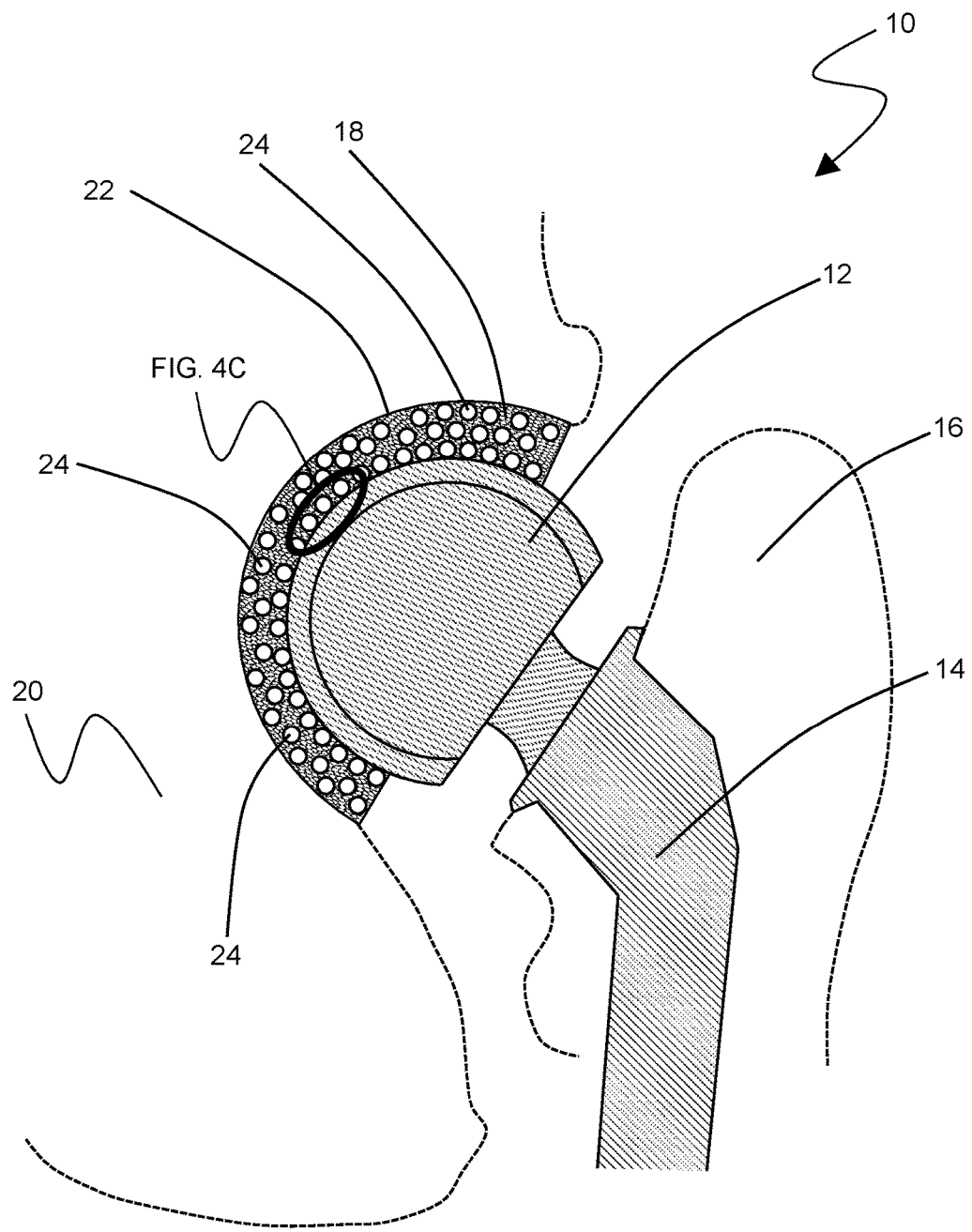
FIG. 4A is a cross-sectional view of the components of a prosthetic hip according to an embodiment of the present invention.
Figure 4B:
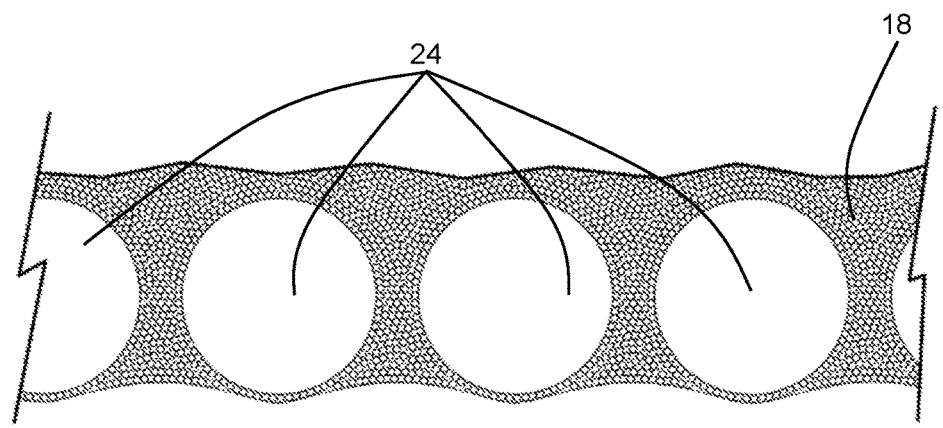
FIG. 4B in an enlarged view of the cross-section of a prosthetic hip component according to an embodiment of the present invention.
Figure 4C:
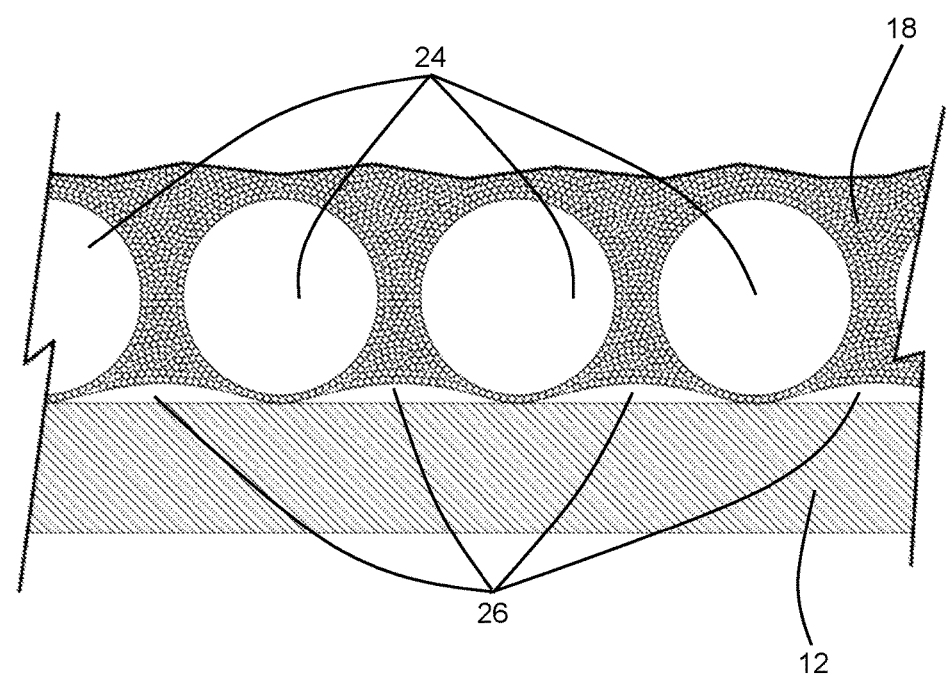
FIG. 4C in an enlarged view of the cross-section of FIG. 4A according to an embodiment of the present invention.

Now referring to FIGS. 4A-4C, according to one embodiment of the present invention, a means to improve the wear characteristics and, therefore, improve the longevity of cup 18 that is comprised chiefly of a polymer material such as polyethylene, ultra high molecular weight polyethylene (UHMWPE), polyether ether ketone (PEEK) and the like or biocompatible polymers such as Teflon and the like, is to infuse the polymer with a plurality of beads 24, spheres or microspheres. Typically beads 24 may be manufactured of glass, ceramic and the like. Beads 24 may have a diameter between 60 microns and 3,000 microns. Beads 24 may be added to the polymer during the manufacturing or molding process. The typical amount of beads 24 to add to the polymer is between 5% and 40% of the total weight of the polymer-bead formulation.

Generally, the force holding the unfilled polymer chains together is a very weak Van Der Waals force. Beads 24 may be coated with a coupling agent or coating such as a silane coupling agent to improve adhesion between beads 24 and the polymer matrix. The coupling agent on beads 24 will bond beads 24 to the polymer matrix with a strong covalent bond thus increasing the wear characteristics of the polymer and increasing the longevity of the prosthetic implant.

Still further, the addition of beads 24 to the polymer during the molding process ensures that the polymer-bead composite material may shrink less than the unfilled polymer material and, therefore, a more accurate composite prosthetic component or cup 18 may be produced. The unfilled polymer contracts as the material cools from an amorphous state to a crystalline state resulting in a shrinkage that must be controlled during the molding process. Beads 24, on the other hand, are in a solid state when introduced to the polymer during the mixing and molding stages. Because beads 24 are in a solid state, they will experience fare less shrinkage than the polymer when the component cools. Because a percentage weight of the polymer has been replaced by beads 24, the polymer-bead composite will naturally experience less shrinkage during the cooling process than the unfilled polymer material. The lower shrinkage rate of the polymer-bead composite also ensures cup 18 will have less internal stresses and therefore be more stable than an unfilled polymer component.

During the bead-polymer molding process, several of beads 24 will make their way to the outer surface of the polymer. Beads 24 will protrude slightly from the surface of the polymer, as illustrated in FIGS. 4B and 4C, due to the polymer shrinking as the polymer changes from an amorphous state to a crystalline state. Further shrinking of the polymer occurs as the polymer cools due to coefficient of thermal contraction. As stated above beads 24 will shrink less than the polymer because beads 24 are in a solid state when introduced to the amorphous polymer. Beads 24 located on the outer surface of the polymer will interact with the mating prosthetic component. In the case of a prosthetic hip, a ball and cup or socket type joint, beads 24 protruding from the outer surface of the polymer socket or cup 18 will interface with the outer surface of ball 12, the ball being generally manufactured of a metallic material or of a ceramic material.

As stated above, beads 24 protruding from the outer surface of the polymer cup 18 will interface with the metallic outer surface of the ball 12 in the prosthetic joint. Beads 24 will act as a shield that will protect the polymer surface of cup 18 from the abrasive wear and adhesive wear created by the metal surface of ball 12 contacting the polymer surface by significantly reducing the contact force between the polymer cup 18 and metal ball 12. Beads 24 will carry much of the contact force between the polymer cup 18 and the metal ball 12 for at least two reasons. First, the young's modulus of bead 24 is approximately 300 times greater than the polymer and therefore would take approximately 300 times the force to compress beads 24 versus the polymer.

Second, beads 24 are extremely scratch resistant due their hardness. The mohs hardness of bead 24 is greater than 5.5 times the mohs hardness of the polymer resulting in improved resistance to abrasion wear. For example, if beads 24 used in the bead-polymer composition are glass beads and the glass beads carry approximately 15% of the load, the polymer surface stress may be reduced by approximately 15%. A 15% reduction in load on the polymer may increase the fatigue life from approximately 40,000 cycles to 400,000 cycles resulting in an increase in the fatigue life of the polymer of ten times or decreases the wear rate by a factor of ten. Beads 24 will interface with metallic ball 12 to prevent metallic ball 12 from interfacing with the polymer directly and likely scratching the softer polymer. The scratching of the polymer may lead to a future deformation of the polymer cup or socket and possible failure of the prosthetic component. The bead-reinforced polymer will have improved compression strength, heat deflection temperature, tensile strength, modulus, wear rate and creep when compared to the unfilled polymer.

Further, the polymer cup 18 wear may be significantly reduced because any abrasive loose particles found within the joint cavity will not scratch beads 24 and will not significantly wear the polymer because the contact force between metal ball 12 and the polymer-bead composite is much less than the contact force between metal ball 12 and polymer cup 18. The fatigue wear will also be less for the metal ball/polymer-bead composite interface versus the metal ball/polymer interface due to the reduced contact force because the reduced contact force reduces the sheer stresses below the polymer surface resulting in a large reduction in fatigue failures.

Break-out friction is another concern of a the prosthetic joint. Typically the break-out friction is the friction required to initiate motion of a body in contact with a surface. In the instance of the prosthetic hip, it is the metal ball/polymer cup interface that experiences a break-out friction when an individual moves the hip joint. Typically, the longer the joint is stationary and the higher the load on the joint (for example, an individual may be standing in the same position and location for a long period) the higher the break-out friction required to move metal ball 12 against polymer cup 18. Damage may be severe to the prosthetic joint if the break-out friction is high and frequent. The reduction in contact force enabled by the polymer-bead composite versus the unfilled polymer helps to ensure a lower break-out friction between the metal ball/polymer-bead composite interface and, in turn lower stresses on the polymer-bead composite which results in less damage to the prosthetic joint and ultimately longer wear life.

Synovial fluid is a viscous, non-Newtonian fluid found in the cavities of synovial joints such as the knee, hip, ankle, shoulder, spine and the like. Synovial fluid is produced by the body and its principal role is to reduce friction between the articular cartilage of a synovial joint. The natural bone structure of the human body ensures that there is an ample flow of synovial fluid in and out of the joint as the joint is loaded and unloaded. Materials used today to create prosthetic joints fit together such there is little to no clearance to allow the passage of synovial fluid into the prosthetic joint. A metal ball used in a ball and socket type joint may have a mating surface to a cup that may be machined and polished to mate precisely with the polymer cup that may also have a precisely machined mating surface. Because both surfaces have been machined so precisely, there is little to no clearance for synovial fluid when the components are mated together to form the joint. This precise machining and lack of clearance between the components may also lead to increased stresses at the leading or trailing edge of the polymer cup as the joint begins to rotate. As the radial clearance approaches zero, the force to move the metal ball relative to the polymer cup may increase exponentially. Due to the squeeze film effect, this leads to increased friction between the two components which leads to increased fatigue and early failure of the components.

In another embodiment of the present invention, beads 24 that protrude from the surface of cup 18 may also aid to lubricate the prosthetic joint. The protruding beads 24 will help to create a gap 26 between the prosthetic metal ball 12 and polymer cup 18 that mimics the gap found in natural bone joints. Gap 26 will allow synovial fluid to both enter and leave the joint area thus reducing the friction between the components. The bead-reinforced polymer will also lower the interfacial temperature between the metal-polymer interface by increasing the thermal conductivity, thereby further reducing friction.

Beads 24 also have a high surface energy of approximately 1000 mN/m versus a polymer such as polyethylene that has a surface energy of approximately 31 mN/m. High surface energies ensure that fluids adhere to the beads through capillary forces and ensure that the lubricating fluid is maintained in the synovial joint during loading and unloading of the joint, thereby still further reducing friction. The typical dry coefficient of friction for the polymer-bead composite is approximately 0.10 to 0.12. The typical coefficient of friction for the polymer-bead composite with lubricating fluid present in the joint is less than 0.10. Reducing the coefficient of friction in the synovial joint reduces the shear forces between the prosthetic components that cause fatigue failure, thereby increasing the wear rate of the prosthetic components.

Further, the height of bead 24 above the outer surface of polymer cup 18 may change as the joint is loaded and unloaded which, in turn, reduces the impact load due to the squeeze film effect. This change in height of beads 24 relative to the outer surface of polymer cup 18 may also work to create a pumping effect to move synovial fluid into and out of the joint. As the prosthetic joint is loaded, the height of beads 24 relative to outer surface of polymer cup 18 is reduced and the synovial fluid is forced out of the joint. When the prosthetic joint is unloaded, the height of beads 24 relative to the joint is increased and the synovial fluid flows back into the joint. The strong hydrogen bonds between the beads and synovial fluid give the beads excellent wetting properties, which may help to retain synovial fluid at the joint interface to further lower friction between the prosthetic components. Synovial fluid entering and exiting the joint also works to flush out any foreign material that may damage the components of the prosthetic joint. This will lead to a decrease in fatigue of the prosthetic materials and ultimately an increase in life of the components and an overall quality of life improvement for the patient.

For example, now referring to the hip joint, when an individual is walking, running or otherwise using the joint, the prosthetic ball and socket or cup are loaded and unloaded many times. In other words, as an individual transitions their weight from one leg to another, the force of the ball against the socket increases. The force of the ball against the socket decrease as an individual transfers their weight to the other leg. Along with the change in forces realized by the prosthetic ball and socket joint, synovial fluid flows in and out of the joint to maintain lubrication between the joint components.

Figure 5A:
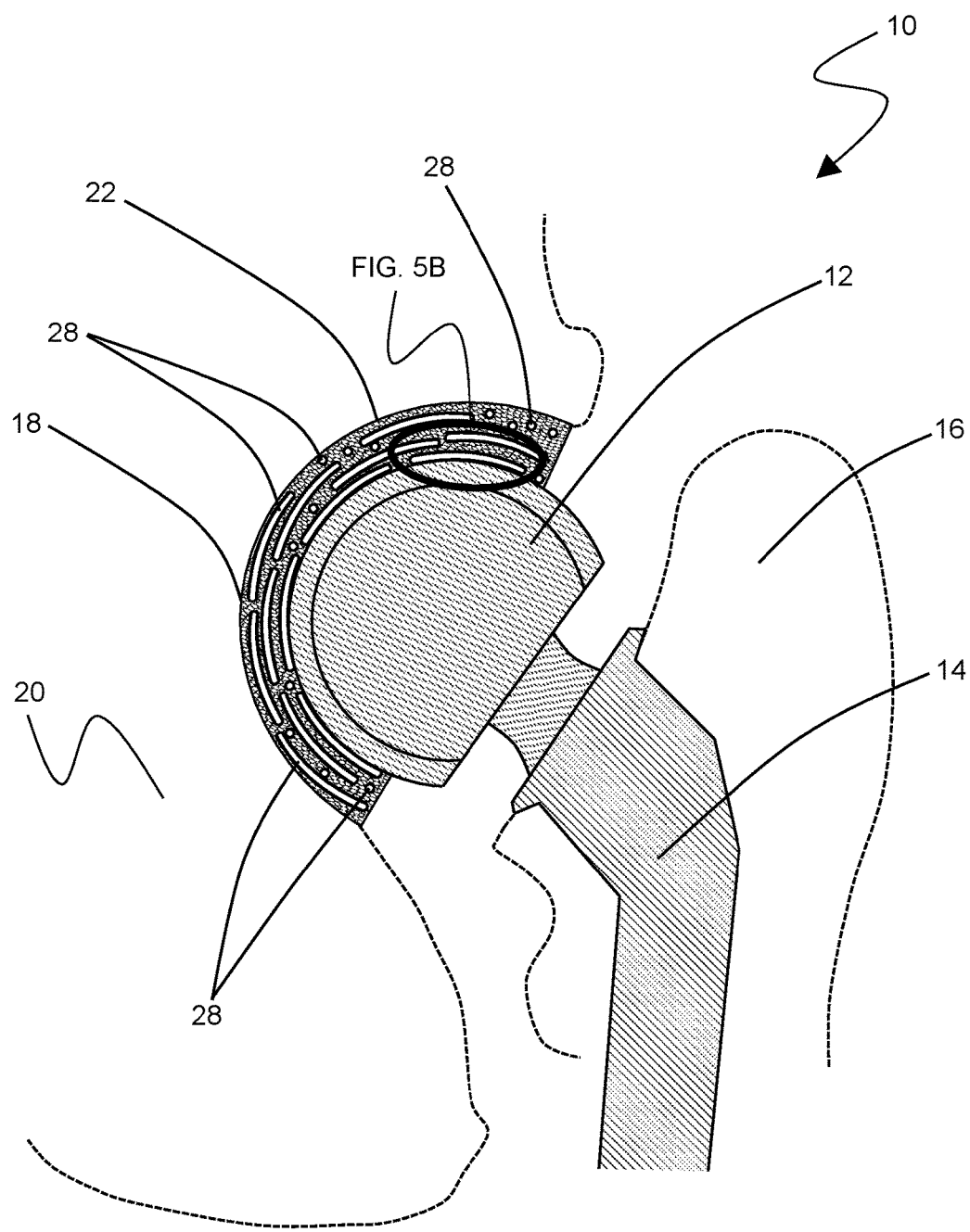
FIG. 5A is a cross-sectional view of the components of a prosthetic hip according to another embodiment of the present invention.
Figure 5B:
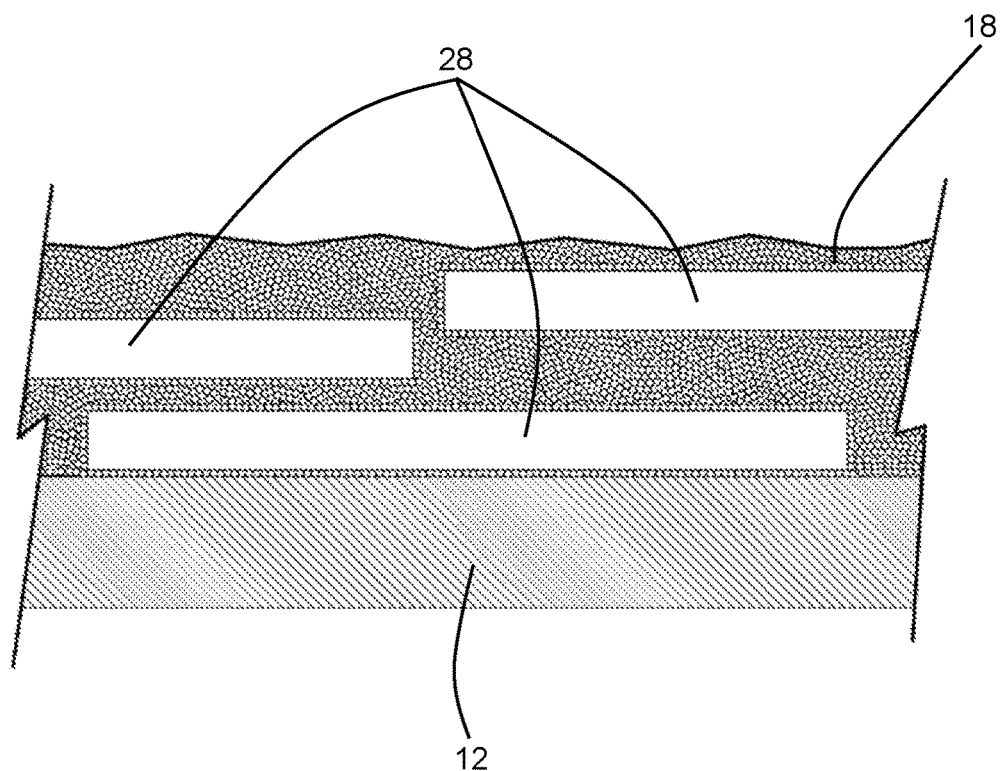
FIG. 5B in an enlarged view of the cross-section of FIG. 5A according to another embodiment of the present invention.
Figure 6A:
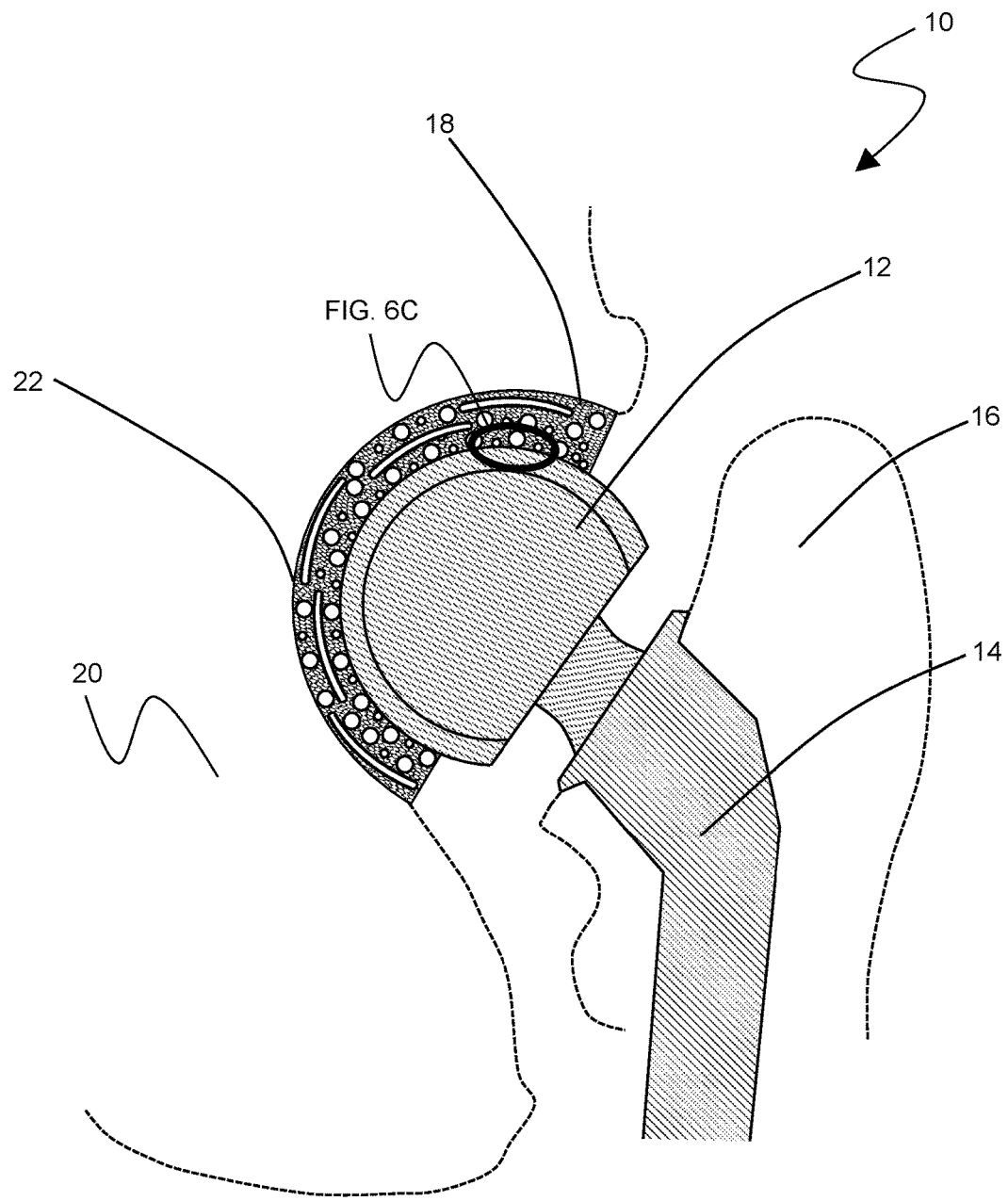
FIG. 6A is a cross-sectional view of the components of a prosthetic hip according to yet another embodiment of the present invention.
Figure 6B:
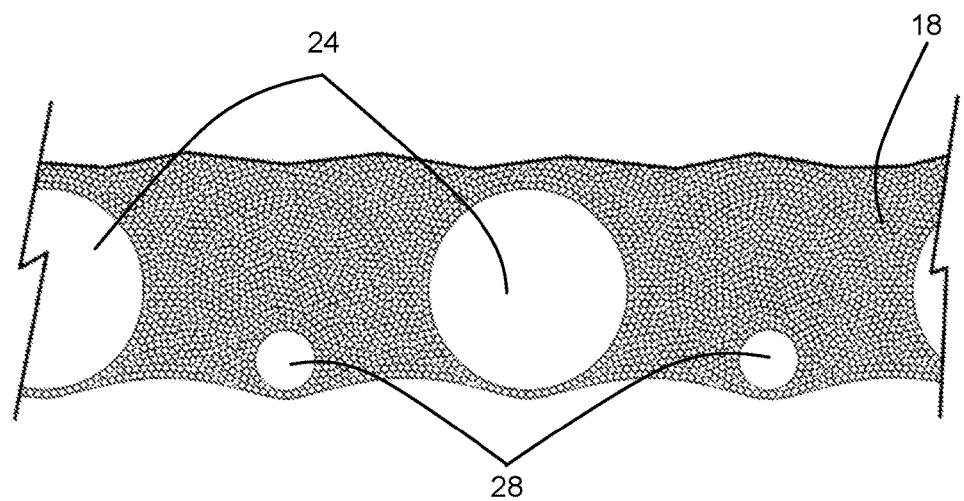
FIG. 6B in an enlarged view of the cross-section of a prosthetic hip component according to yet another embodiment of the present invention.
Figure 6C:
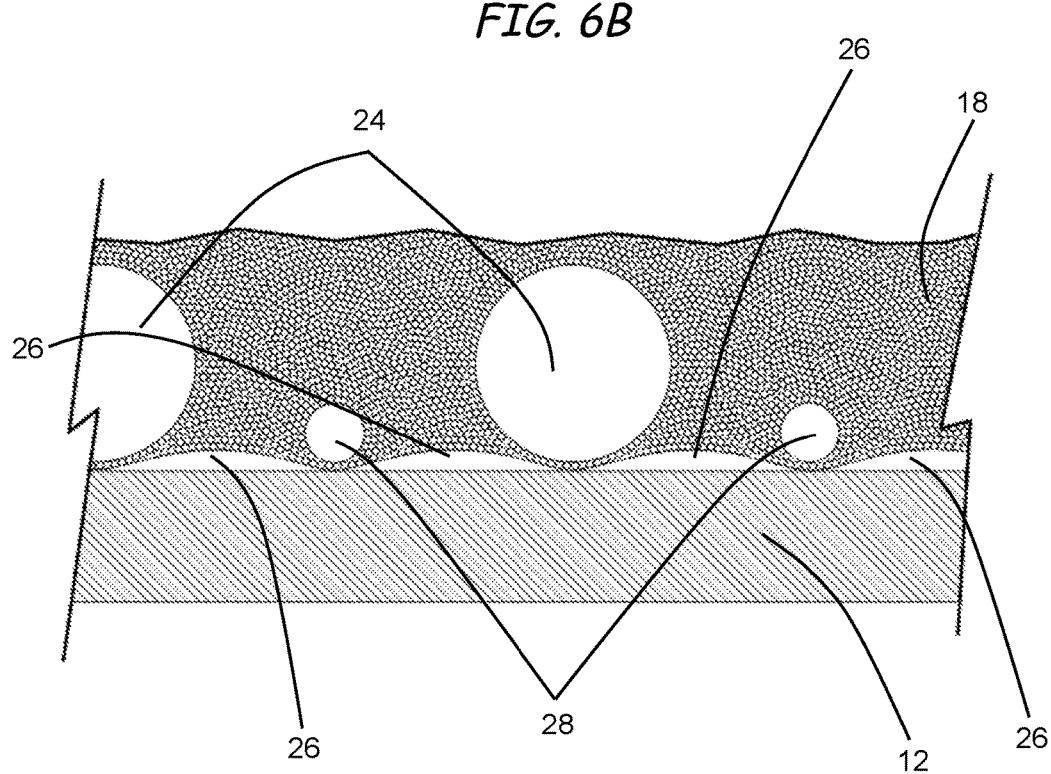
FIG. 6C in an enlarged view of the cross-section of FIG. 6A according to yet another embodiment of the present invention.
Figure 6D:
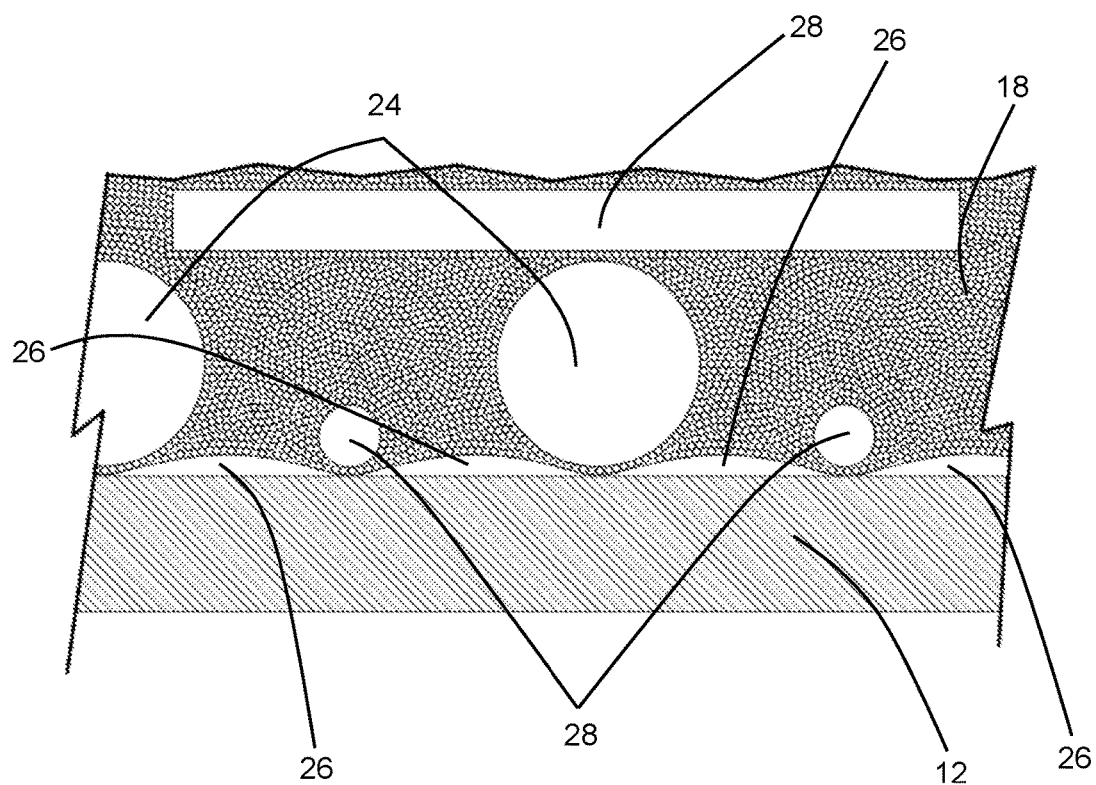
FIG. 6D in an enlarged view of the cross-section of a prosthetic hip component according to yet another embodiment of the present invention.

Referring now to FIGS. 5A and 5B, in yet another embodiment of the present invention, long fiberglass or long glass fibers 28 may be added to the polymer during the mixing and molding processes of the prosthetic components. Long glass fibers 28 may be bundled together to improve strength and may be coated with a coupling agent or coating such as a silane coupling agent to improve adhesion between long glass fibers 28 and the polymer matrix of cup 18. The coupling agent on long glass fibers 28 bond long glass fibers 28 to the polymer matrix of cup 18 with a strong covalent bond thus increasing the wear characteristics of the polymer and increasing the longevity of the prosthetic implant. Long glass fiber reinforced polymer will offer improved tensile strength, shear strength, modulus, creep, crack propagation resistance, heat deflection temperature, fatigue endurance, notched izod under load when compared to an unfilled polymer. For example, a polymer/long glass fiber composite comprised of 60% long glass fiber may increase the tensile strength of the polymer/long glass fiber composite by 500% compared to the unfilled polymer. A polymer/long glass fiber composite comprised of 40% long glass fiber may reduce creep of the polymer/long glass fiber composite by 190% compared to the unfilled polymer. A polymer/long glass fiber composite comprised of 60% long glass fiber may increase the notched izod value of the polymer/long glass fiber composite by 600% compared to the unfilled polymer. Typically, the length of long glass fibers may be from 0.5 mm to 200 mm.

Long glass fibers 28 are much stiffer than the amorphous polymer during the molding process. The tensile modulus of the glass fibers is approximately 73.5 GPa wheel the tensile modulus of the hot amorphous polymer is significantly less than 0.68 GPA. Long glass fibers 28 are over 100 times stiffer than the hot amorphous polymer. During the molding process, long glass fibers 28 will typically align themselves parallel to the surface of polymer cup 18. As the hot amorphous polymer begins to cool, generally at the surface first of cup 18, the cooler portion of the polymer will tend to hold an end of the long glass fibers in place at the outer surface, normal to the outer surface of cup 18, while the remainder of long glass fiber 28 continues to flow in the hot amorphous polymer. The bending moment of the long glass fiber in the hot amorphous polymer is greater than the bending moment of the end of the long glass fiber at the cooler surface. The greater bending moment of the long glass fiber in the hot amorphous polymer will force the end of the long glass fiber at the cool surface out of its normal position to the surface and to align parallel to the surface of the polymer as shown in FIGS. 5A and 5B.

Fatigue wear rate may be significantly reduced by adding long glass fibers 28 to the polymer because long glass fibers 28 inhibit crack nucleation and, more importantly, inhibit any crack propagation because long glass fibers 28 may be able to arrest the growth of any cracks normal to the long glass fiber length. The higher aspect ratio of the reinforcement in long glass fiber/polymer composites facilitates more efficient energy transfer between the fibers and the polymer under impact and dissipates those forces throughout the composite structure rather than localizing the forces in one area of the unfilled polymer. This will lead to a decrease in fatigue of the prosthetic materials used in cup 18 and ultimately an increase in life of the components and an overall quality of life improvement for the patient.

Figure 7:
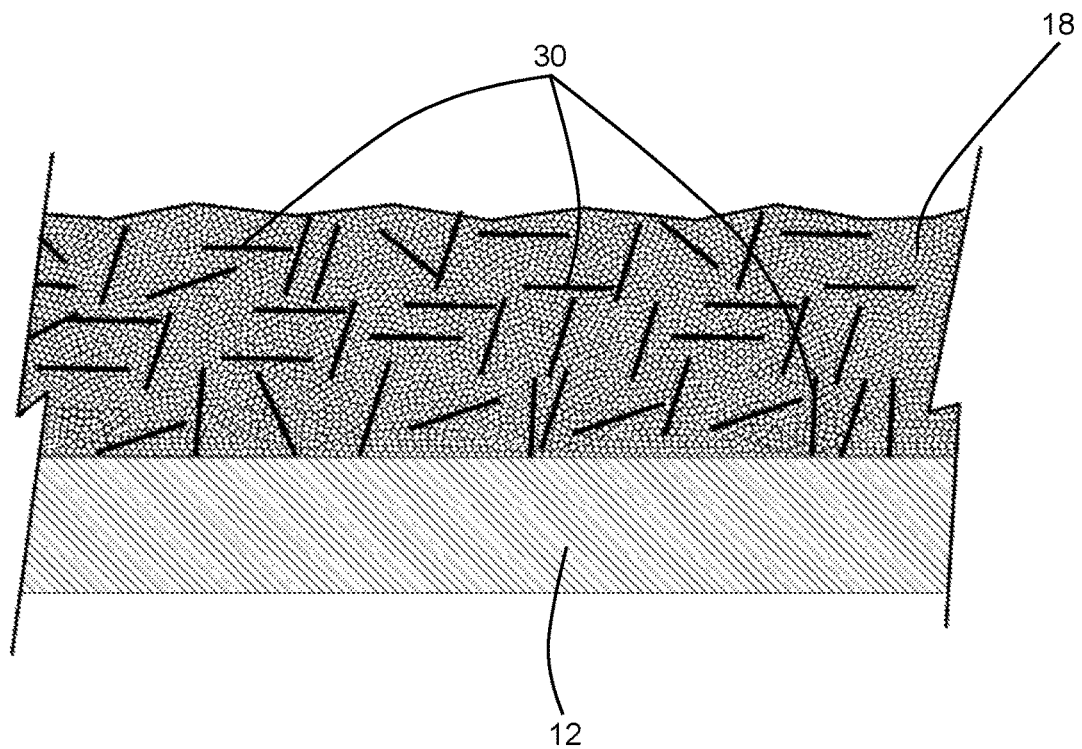
FIG. 7 is a cross-sectional view of one of the components of a prosthetic hip.

The addition of short glass fibers 30 to the polymer during the mixing and molding processes of prosthetic cup 18 is an option to improve the capability of polymer and may be in use today. Short glass fiber 30 reinforced polymer may offer improved strength and fatigue endurance, when compared to an unfilled polymer. Typically the length of short glass fibers 30 are less than 0.5 mm. However, short glass fibers 30 have a major drawback when compared to long glass fibers 28. As state above, glass fibers, whether long or short, are much stiffer than the amorphous polymer during the molding process. During the molding process, long glass fibers 28 will typically align themselves parallel to the surface of the polymer cup 18. Short glass fibers 30 typically do not follow such alignment. The cooler portion of the polymer will tend to hold an end of short glass fibers 30 in place at the surface of cup 18, normal to the surface of cup 18, just as described above for the long glass fibers 28. However, because short glass fibers 30 are shorter in length than long glass fibers 28, there is less of short glass fiber 30 flowing in the hot amorphous polymer. The bending moment of short glass fiber 30 in the hot amorphous polymer is less than or equal to the bending moment of the end of the glass fiber at the cooler surface of cup 18. With no force to change the direction of short glass fiber 30 from normal to the surface of the polymer cup 18, short glass fibers 30 remain normal to the surface of the polymer cup 18. Often many of short glass fibers 30 may align normal to the surface of the polymer during the molding process as illustrated in FIG. 7. Because short glass fibers 30 have a high hardness factor, they may often induce scratches to the metallic surface of the prosthetic ball 12 leading to increased abrasive wear, the introduction of debris into the synovial cavity, lower wear rates and ultimately failure of the prosthetic components. Therefore, it is far more advantageous to use the long glass fiber-polymer composite for the molding of prosthetic components versus the short glass fiber filled polymer.

Figure 14:
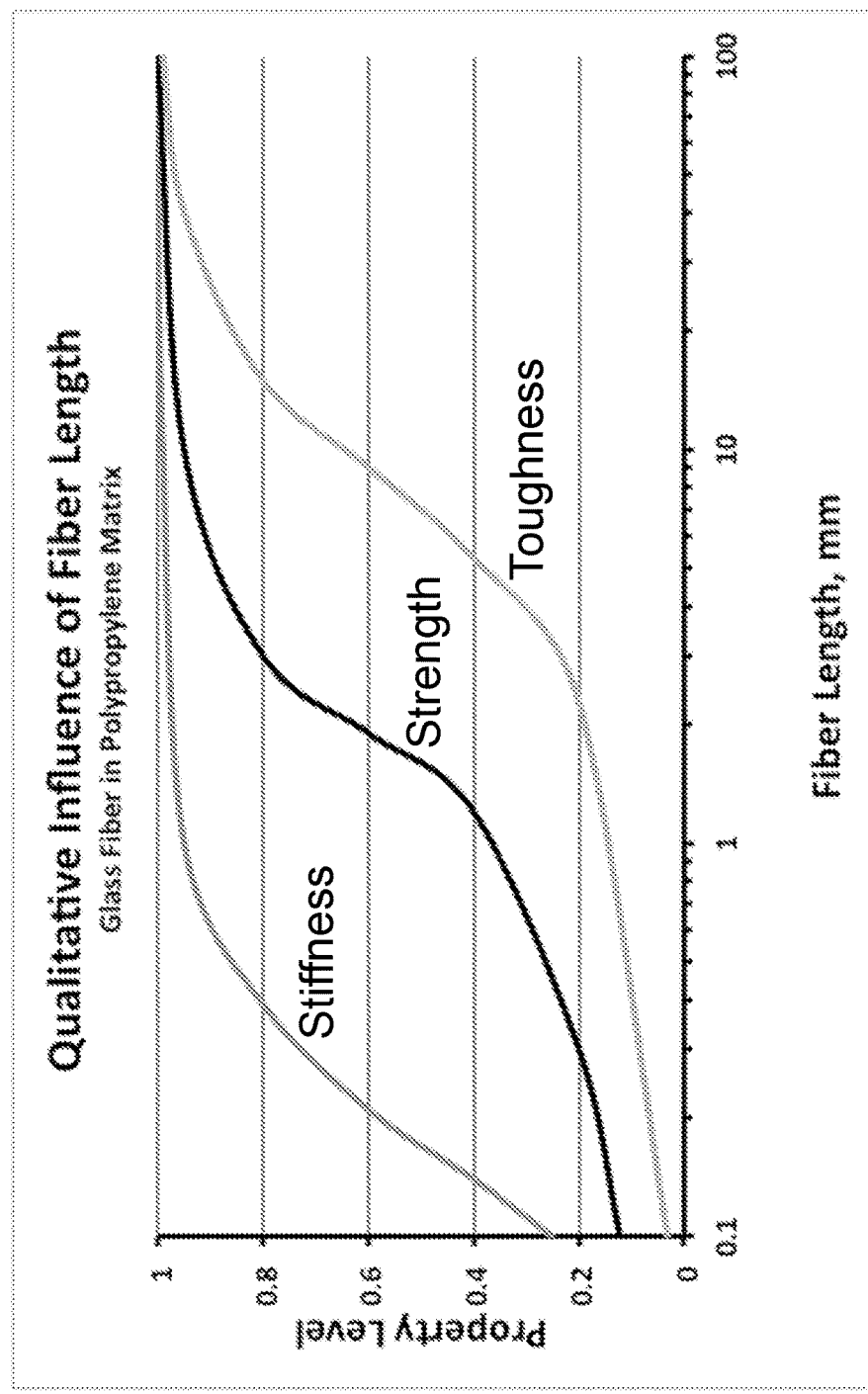
FIG. 14 is a chart that illustrates the impact of glass fiber length in a polypropylene matrix on stiffness, strength and toughness.

Further, the amount of short glass fibers 30 in the polymer-glass fiber composite is much higher than the amount of long glass fibers 28 in the same percentage of glass fibers added to create the polymer-glass fiber composite. This will result in many more short glass fibers 30 included in the polymer-glass fiber composite and ever more short glass fibers 30 that are aligned normal to the polymer surface of cup 18 and the mating component, ball 12, in the joint thereby providing further opportunity to induce scratches and damage to the metal surface of ball 12. Therefore, it is advantageous to use long glass fibers 28 in the polymer-glass fiber composite versus short glass fibers 30 to alleviate any potential scratching and damage to the mating components caused by the short glass fibers. FIG. 14 is a chart that illustrates the impact of glass fiber length in polypropylene matrix on stiffness, strength and toughness. The longer the glass fiber, the higher the stiffness, strength and toughness of the polypropylene leading to improved wear characteristics of the polypropylene.

Figure 15:
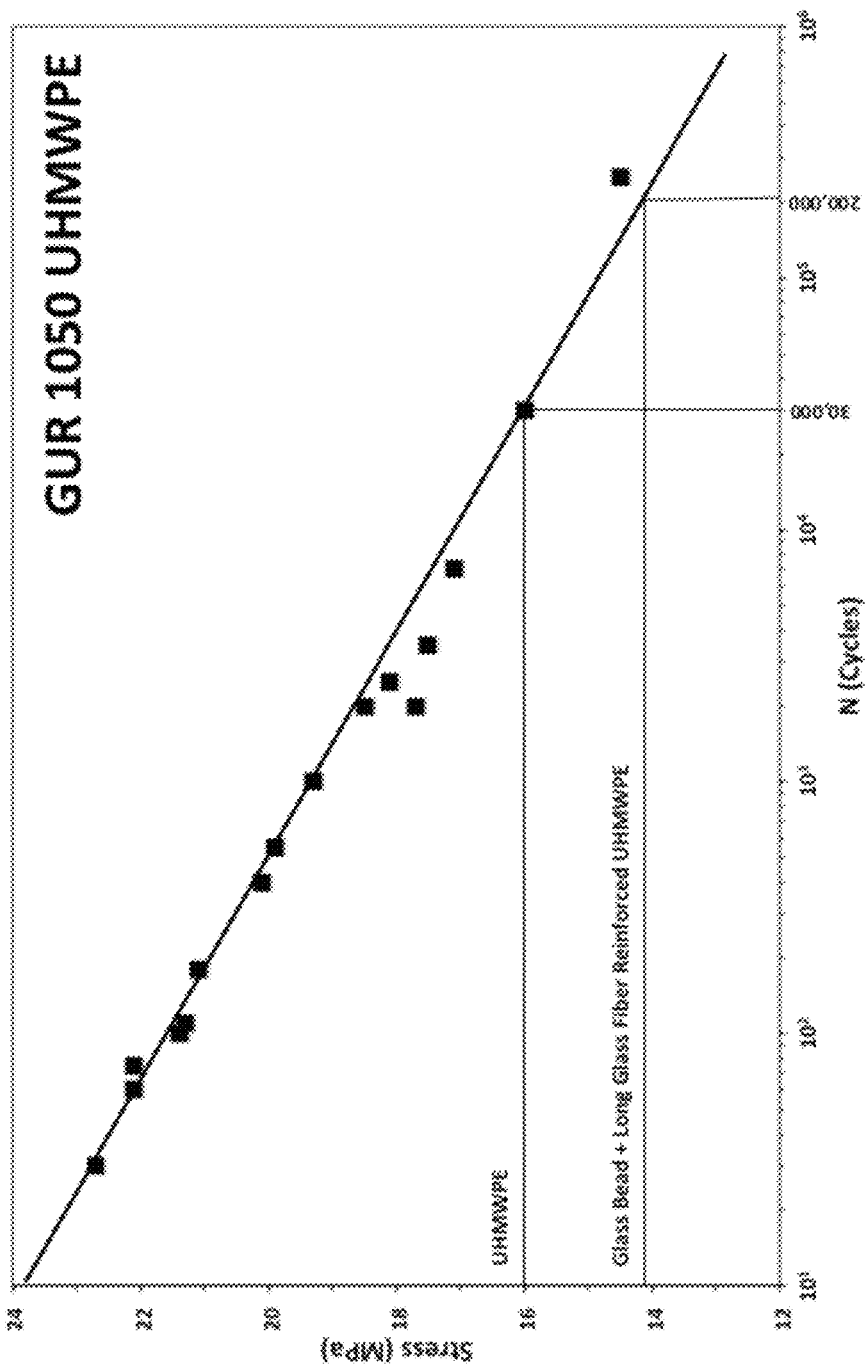
FIG. 15 is a chart that illustrates how the addition of glass beads and the addition of long glass fibers to UHMWPE decreases stress in UHMWPE.

In still another embodiment of the present invention illustrated in FIGS. 6A-6D, beads 24 and long glass fibers 28 may both be added to the polymer of cup 18 to further increase the strength and improve the wear characteristics of the polymer cup 18. As stated above, introducing beads 24, such as glass, beads, ceramic beads and the like into the polymer improves abrasion resistance, compression strength and creep. Introducing long glass fibers 28 into the polymer improves tensile strength, shear strength, creep fatigue strength and heat deflection temperature. The introduction of long glass fibers 28 to the polymer also improves wear rates of the polymer by inhibiting crack nucleation and, more importantly, crack propagation. The polymer-bead-long glass fiber composite improves the over all wear rate of the prosthetic joint over polymer alone which leads to a longer, more comfortable use of the prosthetic joint by the patient. FIG. 15 is a chart that illustrates how the addition of glass beads and long glass fibers to UHMWPE decrease the stress in UHMWPE by approximately 12% versus UHMWPE alone. The reduction in stress by 12% translates to an increase in wear life by six times, from 30,000 cycles to 200,000 cycles.

Long glass fibers 28 may also provide a skeletal network for beads 24 to help ensure the position of a portion of beads 24 just above the surface of the polymer of cup 18. The skeletal network provided by long glass fibers 28 will also help to prevent beads 24 from being pushed into the polymer, ensuring more beads 24 remain at the surface during the molding process of cup 18. Also, any long glass fibers 28 positioned at the surface of the polymer of cup 18 will provide a gap 26 to allow synovial fluid to enter and leave the joint.

The amount of beads 24 and long glass fibers 28 to add to the polymer of cup 18 to create the composite can be varied. Generally, the percentage amount of beads 24 and long glass fibers 28 to be added to create the reinforced polymer-bead-long glass fiber composite may be determined by the loading that a particular joint must endure. For example, the maximum force on the knee joint may be approximately 7.6 times an individual's body weight while in a squatting position. A polymer-bead-long glass fiber composite may include 5% beads, 35% long glass fiber and 60% polymer. The maximum force on the hip joint may be approximately 4.5 times an individual's body weight while walking. A polymer-bead-long glass fiber composite may include 10% beads, 30% long glass fiber and 60% polymer. The maximum force on the ankle joint may be approximately 5.0 times an individual's body weight while walking. A polymer-bead-long glass fiber composite may include 15% beads, 25% long glass fiber and 60% polymer. It is important to note that the above are just sample compositions of the polymer-bead-long glass fiber composite. These compositions are shown as examples only and will be modified to ensure that the highest strength, lowest friction and longest wear rate composites are produced for a particular joint.

A further benefit of the bead-long glass fiber-polymer composite is cost. The typical cost of beads such as glass beads and long glass fibers and bundles are less than the cost of polymers such as UHMWPE. Therefore, the infusion of bead and long glass fibers into the polymer will displace some amount of the polymer as described above thereby decreasing the cost of the bead-long glass fiber-polymer composite versus the polymer alone. Overall wear characteristics of the polymer are improved along with a reduction in cost.

Along with improving the overall wear of the prosthetic joint, the addition of beads 24 and or long glass fibers 28 to the polymer to create cup 18 may also lead to design changes to improve the overall efficiency of the joint. As mentioned above the high friction at the interface of a metal on polymer or metal on ceramic prosthetic joint has forced design changes to limit the interface between the two mating components to lower overall friction in an attempt to improve wear life. These design changes to lower friction have come at a cost to the patient. The patient may realize a loss in range of motion with the newly implanted prosthetic joint. While it may not be an issue for an older patient, many younger patients in the prime of their lives are having to under go arthroplasty to replace a failing joint with a prosthetic joint. Often, these patients are physically active and a loss in range of motion of a particular joint may limit their participation in that activity. The addition of beads 24 and long glass fibers 28 to the polymer of cup 18 may reduce the friction at the joint interface thereby allowing for design improvements in the prosthetic components, such as increasing the interface between cup 18 and ball 12 by making the components larger, to improve the range of motion of the joint for patients and improve their overall quality of life.

FIGS. 8-12 illustrate a knee joint 32 and depict typical prosthetic components used in a knee replacement or arthroplasty. Generally a femoral prosthetic component 34 is configured to be secured to a femur 36. A tibial prosthetic component 38 is configured to be secured to a tibia 40. A spacer 42 is included that is generally secured to tibial component 38 and interfaces with femoral component 34. A patella 44 and a fibula 46 are also included in knee joint 32. Typically, femoral component 34 and tibial component 38 are manufactured of a metallic material such as stainless steel. Spacer 42 is generally manufactured from a polymer such as polyethylene, ultra high molecular weight polyethylene (UHMWPE), polyether ether ketone (PEEK) and the like or biocompatible polymers such as Teflon and the like.

As stated above, the polymer of spacer 42 may include beads 24 (see FIG. 10 and FIGS. 4B and 4C for representative cross-sectional views), long glass fibers 28 (see FIG. 11 and FIG. 5B for a representative cross-sectional view) and a combination of beads 24 and long glass fibers 28 (see FIG. 12 and FIGS. 6B-6D for representative cross-sectional views) to improve the wear characteristics of the polymer. All the improvements to the prosthetic components of the hip joint from the infusion of the polymer with beads and long glass fibers described above will also be realized in the prosthetic components of the knee.

The present invention has been particularly shown and described with reference to the foregoing embodiment, which is merely illustrative of the best modes presently known for carrying out the invention. It should be understood by those skilled in the art that various alternatives to the embodiment of the invention described herein may be employed in practicing the invention without departing from the spirit and scope of the invention as defined in the following claims. It is intended that the following claims define the scope of the invention and that the method within the scope of these claims and their equivalents be covered thereby. This description of the invention should be understood to include all novel and non-obvious combination of elements described herein, and claims may be presented in this or a later application to any novel non-obvious combination of these elements. Moreover, the foregoing embodiment is illustrative, and no single feature or element is essential to all possible combinations that may be claimed in this or a later application.

What is claimed is:

1. A prosthesis for a synovial joint arthroplasty within a human body, said prosthesis including:
a first prosthetic component, said first prosthetic component including a first surface and said first prosthetic component being formed of a plastic compound, said plastic compound including:
a polymer;
a plurality of long glass fibers, said long glass fibers being randomly dispersed throughout said polymer to improve surface fatigue life and inhibit surface crack propagation to said prosthesis and improve wear resistance of said prosthesis, a number of said plurality of long glass fibers configured to protrude outward from said first surface of said first prosthetic component; and
a plurality of beads, said beads being randomly dispersed throughout said polymer to improve surface fatigue life and inhibit surface crack propagation to said prosthesis and improve wear resistance of said prosthesis, a number of said plurality of beads configured to protrude outward from said first surface of said first prosthetic component;
a second prosthetic component, said second prosthetic component including a second surface, said second surface of said second prosthetic component configured to engage said first surface of said first prosthetic component and slide relative to said first surface of said first prosthetic component while contacting said plurality of long glass fibers protruding outward from said first surface of said first prosthetic component and said plurality of beads protruding outward from said first surface of said first prosthetic component; and
a gap, said gap created by the voids between said plurality of beads that protrude outward from said first surface of said first prosthetic component and between said plurality of long glass fibers that protrude outward from said first surface of said first prosthetic component, said gap further disposed between said first surface of said first prosthetic component and said second surface of said second prosthetic component to allow the passage of fluid between said first surface of said first prosthetic component and said second surface of said second prosthetic component.

2. The prosthesis as recited in claim 1, wherein said polymer is ultrahigh molecular weight polyethylene (UHMWPE).

3. The prosthesis as recited in claim 1, wherein said polymer is polyether ether ketone (PEEK).

4. The prosthesis as recited in claim 1, wherein said plurality of beads are glass.

5. The prosthesis as recited in claim 1, wherein said plurality of beads are ceramic.

6. The prosthesis as recited in claim 1, wherein said plurality of beads have a diameter between 60 microns and 3,000 microns.

7. The prosthesis as recited in claim 1, wherein said long glass fibers have a length between 0.4 mm to 200 mm.

8. The prosthesis as recited in claim 1, wherein said plurality of beads are coated with a coupling agent that improves the adhesion between said plurality of beads and said polymer.

9. The prosthesis as recited in claim 1, wherein said long glass fibers are coated with a coupling agent that improves the adhesion between said plurality of long glass fibers and said polymer.

10. A prosthesis for a synovial joint arthroplasty within a human body, said prosthesis including:
    a first prosthetic component, said first prosthetic component including a first surface and said first prosthetic component being formed of a plastic compound, said plastic compound including:
        a polymer;
        a plurality of long glass fibers, said long glass fibers being randomly dispersed throughout said polymer to improve surface fatigue life and inhibit surface crack propagation to said prosthesis and improve wear resistance of said prosthesis, a number of said plurality of long glass fibers configured to protrude outward from said first surface of said first prosthetic component;
    a second prosthetic component, said second prosthetic component including a second surface, said second surface of said second prosthetic component configured to engage said first surface of said first prosthetic component and slide relative to said first surface of said first prosthetic component while contacting said plurality of long glass fibers protruding outward from said first surface of said first prosthetic component; and
    a gap, said gap created by the voids between said plurality of long glass fibers that protrude outward from said first surface of said first prosthetic component, said gap further disposed between said first surface of said first prosthetic component and said second surface of said second prosthetic component to allow the passage of fluid between said first surface of said first prosthetic component and said second surface of said second prosthetic component.

11. The prosthesis as recited in claim 10, wherein said polymer is ultrahigh molecular weight polyethylene (UHM-WPE).

12. The prosthesis as recited in claim 10, wherein said polymer is polyether ether ketone (PEEK).

13. The prosthesis as recited in claim 10, wherein said long glass fibers have a length between 0.4 mm to 200 mm.

14. The prosthesis as recited in claim 10, wherein said long glass fibers are coated with a coupling agent that improves the adhesion between said plurality of long glass fibers and said polymer.

15. A prosthesis for a synovial joint arthroplasty within a human body, said prosthesis including:
    a first prosthetic component, said first prosthetic component including a first surface and said first prosthetic component being formed of a plastic compound, said plastic compound including:
        a polymer;
        a plurality of beads, said beads being randomly dispersed throughout said polymer to improve surface fatigue life and inhibit surface crack propagation to said prosthesis and improve wear resistance of said prosthesis, a number of said plurality of beads configured to protrude outward from said first surface of said first prosthetic component;
    a second prosthetic component, said second prosthetic component including a second surface, said second surface of said second prosthetic component configured to engage said first surface of said first prosthetic component and slide relative to said first surface of said first prosthetic component while contacting said plurality of beads protruding outward from said first surface of said first prosthetic component; and
    a gap, said gap created by the voids between said plurality of beads that protrude outward from said first surface of said first prosthetic component, said gap further disposed between said first surface of said first prosthetic component and said second surface of said second prosthetic component to allow the passage of fluid between said first surface of said first prosthetic component and said second surface of said second prosthetic component.

16. The prosthesis as recited in claim 15, wherein said polymer is ultrahigh molecular weight polyethylene (UHM-WPE).

17. The prosthesis as recited in claim 15, wherein said polymer is polyether ether ketone (PEEK).

18. The prosthesis as recited in claim 15, wherein said plurality of beads are glass.

19. The prosthesis as recited in claim 15, wherein said plurality of beads are ceramic.

20. The prosthesis as recited in claim 15, wherein said plurality of beads have a diameter between 60 microns and 3,000 microns.

21. The prosthesis as recited in claim 15, wherein said plurality of beads are coated with a coupling agent that improves the adhesion between said plurality of beads and said polymer.

* * * * *